United States Patent [19]

Curiel et al.

[11] Patent Number: 5,521,291

[45] Date of Patent: May 28, 1996

[54] CONJUGATES FOR INTRODUCING NUCLEIC ACID INTO HIGHER EUCARYOTIC CELLS

[75] Inventors: David T. Curiel; Ping-chuan Hu, both of Chapel Hill, N.C.; Max L. Birnstiel; Matthew Cotten, both of Vienna, Austria; Ernst Wagner, Langenzersdorf, Austria

[73] Assignees: Boehringer Ingelheim International, GmbH, Germany; Genentech, Inc., South San Francisco, Calif.; University of North Carolina at Chapel Hill, Chapel Hill, N.C.

[21] Appl. No.: 166,899

[22] Filed: Dec. 15, 1993

Related U.S. Application Data

[63] Continuation of Ser. No. 949,205, Sep. 23, 1992, abandoned, which is a continuation-in-part of Ser. No. 864,758, Apr. 7, 1992, abandoned, which is a continuation-in-part of Ser. No. 827,049, Jan. 30, 1992, abandoned, which is a continuation-in-part of Ser. No. 767,787, Sep. 30, 1991, abandoned.

[51] Int. Cl.$^6$ .................. C07K 16/08; A61K 39/42; C12N 7/00; C07H 19/00
[52] U.S. Cl. .................... 530/391.7; 424/147.1; 424/178.1; 424/159.1; 424/93.1; 530/388.3; 536/23.1
[58] Field of Search .................... 424/85.8, 178.1, 424/159.1, 93.1, 147.1; 530/391.7, 388.3; 514/44; 435/235.1; 536/23.1

[56] References Cited

U.S. PATENT DOCUMENTS

| | | | |
|---|---|---|---|
| 5,087,616 | 2/1992 | Myers et al. | 514/21 |
| 5,166,320 | 11/1992 | Wu et al. | 530/395 |
| 5,225,182 | 7/1993 | Sharma | 424/9 |
| 5,240,846 | 8/1993 | Collins et al. | 435/240.1 |

FOREIGN PATENT DOCUMENTS

| | | |
|---|---|---|
| 2012311 | 3/1990 | Canada. |
| WO90/01951 | 3/1990 | WIPO. |
| WO92/06180 | 4/1992 | WIPO. |
| WO92/19749 | 11/1992 | WIPO. |
| WO92/20316 | 11/1992 | WIPO. |
| WO92/22635 | 12/1992 | WIPO. |
| WO93/04701 | 3/1993 | WIPO. |

OTHER PUBLICATIONS

Abrahamson & Rodewald, "Evidence for the Sorting of Endocytic Vesicle Contents during the Receptor-mediated Transport of IgG across the Newborn Rat Intestine", *J. Cell Biol.* 91:270–280 (Oct. 1981).

Akopian et al., "Sequence of an avian adenovirus (CELO) DNA fragment (0–11.2%)", *Nucl. Acids Res.* 19:424 (1990).

American Type Culture Collection, "Catalogue of Animal Viruses and Antisera, Chlamydiae and Rickettsiae", Buck, C. & Paulino, G., eds., *Sixth Ed.*:1–17 (1990).

Anderson et al., "Specific Binding of $^{125}$I–Human Interferon–γ to High Affinity Receptors on Human Fibroblasts", *J. Biol. Chem.* 257:11301–11304 (Oct. 10, 1982).

Ansardi et al., "Coinfection with Recombinant Vaccinia Viruses Expressing Poliovirus P1 and P3 Proteins Results in Polyprotein Processing and Formation of Empty Capsid Structures", *J. Virol.* 65:2088–2092 (Apr. 1991).

Armentano et al., "Effect of Internal Viral Sequences on the Utility of Retroviral Vectors", *J. Virol.* 61:1647–1650 (May 1987).

Armentano et al., "Expression of human factor IX in rabbit hepatocytes by retrovirus-mediated gene transfer: Potential for gene therapy of hemophilia B", *Proc. Natl. Acad. Sci. USA* 87:6141–6145 (Aug. 1990).

Asada–Kubota et al., "Binding and internalization of $^{125}$I–glucagon in hepatocytes of intact mouse liver. An autoradiographic study", *Exp. Path.* 23:95–101 (1983).

Ascoli & Puett, "Inhibition of the Degradation of Receptor--bound Human Choriogonadotropin by Lysosomotropic Agents, Protease Inhibitors, and Metabolic Inhibitors", *J. Biol. Chem.* 253:7832–7838 (Nov. 10, 1978).

Horvath & Weber, "Nonpermissivity of Human Peripheral Blood Lymphocytes to Adenovirus Type 2 Infection", *J. Virol.* 62:341–345 (Jan. 1988).

Hosang & Shooter, "The internalization of nerve growth factor by high-affinity receptors on pheochromocytoma PC12 cells", *EMBO J.* 6:1197–1202 (1987).

Hu et al., "Surface Parasitism by *Mycoplasma pneumoniae* of Respiratory Epithelium", *J. of Exp. Med.* 145:1328–1343 (1977).

Helenius et al., "Viruses as Tools in Drug Delivery", *Annals NY Acad Sci* 507:1–6 (1987).

Hizuka et al., "Polypeptide Hormone Degradation and Receptor Regulation are Coupled to Ligand Internalization", *J. Biol. Chem.* 256:4591–4597 (May 10, 1981).

Holland, J., "Defective Viral Genomes", *Virology*, 2nd Ed., edited by B. N. Fields, D. M. Knipe et al., Raven Press Ltd., NY, 151–165 (1990).

Hazinksi et al., "Localization and Induced Expression of Fusion Genes in the Rat Lung", *Am. J. Respir. Cell Mol. Biol.* 4:206–209 (1991).

Hearst & Thiry, "The photoinactivation of an RNA animal virus, vesicular stomatitis virus, with the aid of newly synthesized psoralen derivatives", *Nucl. Acids Res.* 4:1339–1347 (1977).

Heldin et al., "Interaction of a Platelet–derived Growth Factor with Its Fibroblast Receptor", *J. Biol. Chem.* 257:4216–4221 (Apr. 25, 1982).

(List continued on next page.)

*Primary Examiner*—Lila Feisee
*Attorney, Agent, or Firm*—Sterne, Kessler, Goldstein & Fox

[57] ABSTRACT

Conjugates in which a virus is bound via an antibody to a substance having an affinity for nucleic acid, for transporting gene constructs into higher eucaryotic cells. Complexes of the conjugates and nucleic acid are internalized in the cell, whilst the virus as part of the complex brings about the internalization and the release of the contents of the endosomes, in which the complexes are located after entering the cell. Pharmaceutical preparations in which the nucleic acid is a therapeutically active gene construct, particularly for use in gene therapy.

15 Claims, 18 Drawing Sheets

OTHER PUBLICATIONS

Goldstein & Brown, "Lipoprotein Receptors: Genetic Defense Against Atherosclerosis", *Clin. Res.* 30:417–426 (1982).

Green et al., "Mutational Analysis of HIV–1 Tat Minimal Domain Peptides: Identification of Trans–Dominant Mutants That Suppress HIV–LTR–Driven Gene Expression", *Cell* 58:215–223 (Jul. 14, 1989).

Harris et al., "Gene Transfer to Primary Airway Epithelial Cells Employing Molecular Conjugate vectors", *Clinical Research Abstracts* 40:317A (Apr. 1992).

Ginsberg et al., "Picornaviruses", *Microbiology*, 3rd Edition, Ed. by Davis, B. D. et al., Harper & Row, Picornaviruses, 1095–1117 (1980).

Goldstein et al., "Binding site on macrophages that mediates uptake and degradation of acetylated low densityy lipoprotein, producing massive cholesterol deposition", *Proc. Natl. Acad. Sci. USA* 76:333–337 (Jan. 1979).

Goldstein et al., "What should be called a lectin?", *Nature* 285:66 (May 8, 1980).

Fujiwara et al., "Novel Preparation Method of Immunogen for Hydrophobic Hapten, Enzyme Immunoassay for Daunomycin and Adriamycin", *J. Immunol. Meth.* 45:195–203 (1981).

Gaynor & Berk, "Cis–Acting Induction of Adenovirus Transcription", *Cell* 33:683–693 (Jul. 1983).

Geysen et al., "Use of a peptide synthesis to probe viral antigens for epitopes to a resolution of a single amino acid", *Proc. Natl. Acad. Sci. USA* 81:3998–4002 (Jul. 1984).

Fernández–Puentes & Carrasco, "Viral Infection Permeabilizes Mammalian Cells to Protein Toxins", *Cell* 20:769–775 (Jul. 1980).

FitzGerald et al., "Adenovirus–Induced Release of Epidermal Growth Factor and Pseudomonas Toxin into the Cytosol of KB Cells during Receptor–Mediated Endocytosis", *Cell* 32:607–617 (Feb. 1983).

Folk & Chung, "Transglutaminases", *Methods in Enzym.* 113:358–375 (1985).

Dhawan et al., "Systemic Delivery of Human Growth Hormone by Injection of Genetically Engineered Myoblasts", *Science* 254:1509–1512 (Dec. 6, 1991).

Eaton et al., "Construction and Characterization of an Active Factor VIII Variant Lacking the Central One–Third of the Molecule", *Biochem.* 25:8343–8347 (Dec. 30, 1986).

Felgner et al., "Lipofection: A highly efficient lipid mediated DNA–transcription procedure", *Proc. Natl. Acad. Sci. USA* 84:7413–7417 (Nov. 1987).

De Wet et al., "Firefly Luciferase Gene: Structure and Expression in Mammalian Cells", *Mol. & Cell. Biol.* 7:725–737 (Feb. 1987).

Defer et al., "Human Adenovirus–Host Cell Interactions: Comparative Study with Members of Subgroups B and C", *J. Virology* 64:3661–3673 (Aug. 1990).

Department of Health & Human Services/Public Health Service: Food & Drug Administration Grant Application, "Development of a *Mycoplasma pneumoniae*–Adenovirus Hybrid Oral Vaccine", (Funded: Jan. 19, 1989–Jan. 18, 1993).

Curiel, D. et al., "In vivo Gene Transfer to Airway Epithelium Employing Molecular Conjugate Vectors", *Cold Spirng Harbor Gene Therapy Conference* (Jul. 1992).

Curiel, T. et al. "Foreign Gene Expression in EBV–Transformed B–Cells: Potential for the Development of Novel CTL Target Cells", *J. Cell Biochem. Suppl.* 60:Q407 (1992).

Davidson & Hassell, "Overproduction of Polyomavirus Middle T Antigen in Mammalian Cells through the Use of an Adenovirus Vector", *J. Virol.* 61:1226–1239 (Apr. 1987).

Curiel D. et al., "Adenovirus enhancement of transferrin––polylysine–mediated gene delivery", *Proc. Natl. Acad. Sci. USA* 88:8850–8854 (Oct. 1991).

Curiel D. et al., "Gene Transfer to Respiratory Epithelial Cells via the Receptor–mediated Endocytosis Pathway", *Am. J. Resp. Cell. Mol. Biol.* 6:247–252 (1992).

Curiel D. et al., "High–Efficiency Gene Transfer Mediated by Adenovirus Coupled to DNA–Polylysine Complexes", *Human Gene Therapy* 3:147–154 (Apr. 1992).

Collis et al., "Definition of the minimal requirements within the human β–globin gene and the dominant control region for high level expression", *EMBO J.* 9:233–240 (1990).

Cotten et al., "Transferrin–polycation–mediated introduction of DNA into human leukemic cells: Stimulation by agents that affect the survival of transfected DNA or modulate transferrin receptor levels", *Proc. Natl. Acad. Sci. USA* 87:4033–4037 (Jun. 1990).

Cotten et al., "High–efficiency receptor–mediated delivery of small and large (48 kilobase gene constructs using the endosome–disruption activity of defective or chemically inactivated adenovirus particles", *Proc. Natl. Acad. Sci. USA* 89:6094–6098 (Jul. 1992).

Ciliberto et al., "Cell–Specific Expression of a Transfected Human $\alpha_1$–Antitrypsin Gene", *Cell* 41:531–540 (Jun. 1985).

Clarke, D. D. et al., "The Incorporation of Amines into Protein", *Arch. Biochem. & Biophys.* 79:338–354 (1959).

Clarke, L. L. et al., "Defective Epithelial Chloride Transport in a Gene–Targeted Mouse Model of Cystic Fibrosis", *Science* 257:1125–1128 (Aug. 21, 1992).

Berkner & Sharp, "Generation of adenovirus by transfection of plasmids", *Nucl. Acids Res.* 11:6003–6020 (1983).

Berns, K., "Parvoviridae and Their Replication", *Virology*, 2nd edition, Ed. by Fields, B. N., Knipe, D. M. et al., Raven Press Ltd., N.Y., 1743–1763 (1990).

Bragg et al., "Isolation and Identification of Adenovirus 127, The Causative Agent of Egg Drop Syndrome (EDS), From Commercial Laying Hens In South Africa", *Onderstepoort J. vet. Res.* 58:309–310 (1991).

Carpenter, G., "Properties of the Receptor for Epidermal Growth Factor", *Cell*, 37:357–358 (Jun. 1984).

Chardonnet & Dales, "Early Events in the Interaction of Adenoviruses with HeLa Cells", *Virology* 40:462–477 (1970).

Cheng et al., "Receptor–mediated uptake of 3,3',5–triiodo–L–thyronine by cultured fibroblasts", *Proc. Natl. Acad. Sci. USA* 77:3425–3429 (Jun. 1980).

Ashwell & Harford, "Carbohydrate–Specific Receptors of the Liver", *Ann. Rev. Biochem.* 51:531–554 (1982).

Barr & Leiden, "Systemic Delivery of Recombinant Proteins by Genetically Modified Myoblasts",*Science* 254:1507–1509 (Dec. 6, 1991).

Baum & Paulson, "Sialyloligosaccharides of the respiratory epithelium in the selection of human influenza virus receptor specificity", *Acta Histochem. Suppl.* 40:35–38 (1990).

Huang, A., "The Role of Defective Interfering (DI) Particles in Viral Infection", *The Molecular Basis of Viral Replication*, Ed. by Bercoff, R. P., Plenum Press, N.Y. & London, 191–194 (1987).

Imamura et al., "Expression of Tumor Necrosis Factor Receptors on Human Monocytes and Internalization of Receptor Bound Ligand", *J. Immunology* 139:2989–2992 (Nov. 1, 1987).

Imperiale et al., "Common Control of the Heat Shock Gene and early Adenovirus Genes: Evidence for a Cellular E1A–like Acitivity", *Molec. & Cell. Biol.* 4:867–874 (May 1984).

Inamine et al., "Analysis of the nucleotide sequence of the P1 operon of *Mycoplasma pneumoniae*", *Gene* 73:175–183 (1988).

Iwanij, V., "The Use of Liver Transglutaminase for Protein Labeling", *Eur. J. Biochem.* 80:359–368 (1977).

Jacobs et al., "Binding Sites of Attachment–Inhibiting Monoclonal Antibodies and Antibodies from Patients on Peptide Fragments of the *Mycoplasma pneumoniae* Adhesin", *Infection & Immunity* 57:685–688 (Mar. 1989).

Jung et al., "Biological Activity of the Antitumor Protein Neocarzinostatin coupled to a monoclonal antibody by N–Succinimidyl 3–(2–pyridyldithio)–propionate", *Biochem. & Biophys. Res. Comm.* 101:599–606 (Jul. 30, 1981).

Kaplan & Nielsen, "Analysis of Macrophage Surface Receptors", *J. Biol. Chem.* 254:7323–7328 (Aug. 10, 1979).

Kasid et al., "Human gene transfer: Characterization of human tumor–infiltrating lymphocytes as vehicles for retroviral–mediated gene transfer in man", *Proc. Natl. Acad. Sci. USA* 87:473–477 (Jan. 1990).

Keller et al., "Expression of a foreign gene in myeloid and lymphoid cells derived from multipotent haematopoietic precursors", *Nature* 318:149–154 (Nov. 14, 1985).

Klausner et al., "Binding of apotransferrin to K562 cells: Explanation of the transferrin cycle", *Proc. Natl. Acad. Sci. USA* 80:2263–2266 (Apr. 1983).

Klausner et al., "Receptor–mediated Endocytosis of Transferrin in K562 Cells", *J. Biol. Chem.* 258:4715–4724 (Apr. 25, 1983).

Kühn & Kraehenbuhl, "The sacrificial receptor–translocation of polymeric IgA across epithelia", *Trends Biochem. Sci.* 7:299–302 (Aug. 1982).

Kurachi & Davie, "Isolation and characterization of a cDNA coding for human factor IX", *Proc. Natl. Acad. Sci. USA* 79:6461–6464 (Nov. 1982).

Lapidot & Loyter, "Fusion–Mediated Microinjection of Liposome–Enclosed DNA into Cultured Cells with the Aid of Influenza Virus Glycoproteins", *Experimental Cell Res.* 189:241–246 (1990).

Laver et al., "Purification and Properties of Chick Embryo Lethal Orphan Virus (an Avian Adenovirus)", *Virology* 45:598–614 (1971).

Lim & Chae, "A Simple Assay for DNA Transfection by Incubation of the Cells in Culture Dishes with Substrates for Beta–Galactosidase", *BioTechniques* 7:576–579 (1989).

Lori et al., "Non Retroviral Delivery of Protective Genes Against HIV–1", *Cold Spring Harbor Gene Therapy Conference* (Jul. 1992).

MacGregor & Caskey, "Construction of plasmids that express *E. coli* β–galactosidase in mammalian cells", *Nucl. Acids Res.* 17:2365 (1989).

Malim et al., "Functional Dissection of the HIV–1 Rev Trans–Activator–Derivation of a Trans–Dominant Repressor or Rev Function", *Cell* 58:205–214 (Jul. 14, 1989).

Marsh & Helenius, "Virus Entry into Animal Cells", *Adv. in Virus Res.* 36:107–151 (1989).

Marshall, S., "Kinetics of Insulin Receptor Internalization and Recycling in Adipocytes", *J. Biol. Chem.* 260:4136–4144 (Apr. 10, 1985).

Massagué and Kelly, "Internalization of Transforming Growth Factor–β and Its Receptor in BALB/c 3T3 Fibroblasts", *J. Cell. Phys.* 128:216–222 (1986).

Maurer, R., "Cationic Liposome–Mediated Transfection of Primary Cultures of Rat Pituitary Cells", *Focus* (11:2):25–27 (1989).

McClure et al., "The pH independence of mammalian retrovirus infection", *J. Gen. Virol.* 71:767–773 (1990).

Mellman & Plutner, "Internalization and Degradation of Macrophage Fc Receptors Bound to Polyvalent Immune Complexes", *J. Cell. Biol.* 98:1170–1177 (Apr. 1984).

Mizel et al. "The Interleukin 1 Receptor. Dynamics of Interleukin 1 Binding and Internalization in T Cells and Fibroblasts", *J. Immunol.* 138:2906–2912 (May 1, 1987).

Morin et al., "Recombinant adenovirus induces antibody response to hepatitis B virus surface antigen in hamsters", *Proc. Natl. Acad. Sci. USA* 84:4626–4630 (Jul. 1987).

Nevins, J., "Mechanism of Activation of Early Viral Transcription by the Adenovirus E1A Gene Product", *Cell* 26:213–220 (Oct. 1981).

Otero & Carrasco, "Proteins are Cointernalized with Virion Particles during Early Infection", *Virology* 160:75–80 (1987).

Parente et al., "Mechanism of Leakage of Phospholipid Vesicle Contents Induced by the Peptide GALA", *Biochem.* 29:8720–8728 (1990).

Piazza et al., "Attachment of Influenza A Virus to Ferret Tracheal Epithelium at Different Maturational Stages", *Am. J. Resp. Cell. Mol. Biol.* 4:82–87 (1991).

Ponder et al., "Mouse hepatocytes migrate to liver parenchyma and function indefinitely after intrasplenic transplantation", *Proc. Natl. Acad. Sci. USA* 88:1217–1221 (Feb. 1991).

Posner et al., "Effect of Colchicine on the Uptake of Prolactin and Insulin into Golgi Fractions of Rat Liver", *J. Cell. Biol.* 93:560–567 (Jun. 1982).

Precious & Russell, "Growth, Purification and Titration of Adenoviruses", *Virology*, ed. Mahy, B. W. J., IRL Press, Oxford, Washington, D.C., 193–205 (1985).

Rafalski et al., "Phospholipid Interactions of Synthetic Peptides Representing the N–Terminus of HIV gp41", *Biochem.* 29:7917–7922 (1990).Reece et al., "Pathogenicity studies with a strain of fowl adenovirus serotype 8 (VRI–33) in chickens", *Austral. Vet. J.* 64:365–367 (Dec. 1987).

Riordan et al., "Identification of the Cystic Fibrosis Gene: Cloning and Characterization of the Complementray DNA", *Science* 245:1066–1073 (Sep. 8, 1989).

Roberts et al, "Three–Dimensional Structure of the Adenovirus Major Coat Protein Hexon", *Science* 232:1148–1151 (May 30, 1986).

Rosenberg et al., "Immunization of Cancer Patients Using Autologous Cancer Cells Modified by Insertion of the Gene for Interleukin–2", *Human Gene Therapy* 3:75–90 (1992).

Rosenfeld et al., "Adenovirus–mediated transfer of the normal human cystic fibrosis transmembrane conductance regulator (CFTR) cDNA to freshly isolated normal and cystic fibrosis respiratory epithelium", *Clinical Res.* 40:317A (1992).

Russell et al., "Monoclonal Antibodies against Adenovirus Type 5: Preparation and Preliminary Characterization", *J. gen. Virol.* 56:393–408 (1981).

Sambrook, J., "Expression of Cloned Genes in Cultured Mammalian Cells", *J. Molec. Cloning, 2nd edition,* vol. 3:16.39–16.40 (1989)

Schalch et al., "Interaction of Insulin–Like Growth Factor I/Somatomedin–C with Cultured Rat Chondrocytes: Receptor Binding and Internalization", *Endocr.* 118:1590–1597 (1986).

Sennett & Rosenberg, "Transmembrane Transport of Cobalamin in Prokaryotic and Eukaryotic Cells", *Am. Rev. Biochem.* 50:1053–1086 (1981).

Seth et al., "Evidence that the Penton Base of Adenovirus is Involved in Potentiation of Toxicity of Pseudomonas Exotoxin Conjugated to Epidermal Growth Factor", *Mol. & Cell. Biol.* 4:1528–1533 (Aug. 1984).

Seth et al., "Pathway of Adenovirus Entry into Cells", *Virus Attachment and Entry into Cells,* Crowell & Lonberg–Holm, eds., Am. Soc. for Microbiol., Washington, D.C., 191–195 (1986).

Severne et al., "Metal binding 'finger' structures in the glucocorticoid receptor defined by site–directed mutagenesis", *EMBO J.* 7:2503–2508 (1988).

Shepherd, V., "Intracellular Pathways and mechanisms of sorting in receptor–mediated endocytosis", *TiPs* 10:458–462 (Nov. 1989).

Silver & Anderson, "Interaction of Human Adenovirus Serotype 2 with Human Lymphoid Cells", *Virology* 165:377–387 (1988).

Sly & Fisher, "The Phosphomannosyl Recognition System for Intracellular and Intercellular Transport of Lysosomal Enzymes", *J. Cell. Biochem.* 18:67–85 (1982).

Smith & Cantrell, "Interleukin 2 regulates its own receptors", *Proc. Natl. Acad. Sci. USA* 82:864–868 (Feb. 1985).

Stahl et al., "Evidence for receptor–mediated binding of glycoproteins, glycoconjugates, and lysosomal glycosidases by alveolar macrophages", *Proc. Natl. Acad. Sci. USA* 75:1399–1403 (Mar. 1978).

Strauss & Jaenisch, "Molecular complementation of a collagen mutation in mammalian cells using yeast artificial chromosomes", *EMBO J.* 11:417–422 (1992).

Subbarao et al., "pH–Dependent Bilayer Destabilization by an Amphipathic Peptide", *Biochem.* 26:2964–2972 (1987).

Sullenger et al., "Overexpression of TAR Sequences Renders Cells Resistant to Human Immunodeficiency Virus Replication", *Cell* 63:601–608 (Nov. 2, 1990).

Svensson, U., "Role of Vesicles During Adenovirus 2 Internalization into HeLa Cells", *J. Virol.* 55:442'449 (Aug. 1985).

Takase et al., "Avian Adenovirus Isolated from Pigeons Affected with Inclusion Body Hepatitis", *Jpn. J. Vet. Sci.* 52:207–215 (1990).

Trono et al., "HIV–1 Gag Mutants Can Dominantly Interfere with the Replication of the Wild–Type Virus", *Cell* 59:113–120 (Oct. 6, 1989).

Uchida et al., "Distribution of Neuraminidase in Arthrobacter and Its Purification by Affinity Chromatography", *J. Biochem.* 82:1425–1433 (1977).

Urakawa et al., "Synthesis of Immunogenic, but Non–infectious, Polivirus Particles in Insect Cells by a Baculovirus Expression Vector", *J. gen. Virol.* 70:1453–1463 (1989).

Valerio et al., "Cloning of human adenosine deaminase cDNA and expression in mouse cells", *Gene* 31:147–153 (1984).

Wagner et al., "Transferrin–polycation conjugates as carriers for DNA uptake into cells", *Proc. Natl. Acad. Sci. USA* 87:3410–3414 (May 1990).

Wagner et al., "DNA–Binding Transferrin Conjugates as Functional Gene–Delivery Agents: Synthesis by Linkage of Polylysine or Ethidium Homodimer to the Transferrin Carbohydrate Moiety", *Bioconjugate Chem.* 2:226–231 (1991).

Wagner et al., "Transferrin–polycation–DNA complexes: The effect of polycations on the structure of the complex and DNA delivery to cells", *Proc. Natl. Acad. Sci. USA* 88:4255–4359 (May 1991).

Walker et al., "Long–term culture and fine specificity of human cytotoxic T–lymphocyte clones reactive with human immmunodeficiency virus type 1", *Proc. Natl. Acad. Sci. USA* 86:9514–9518 (Dec. 1989).

Walker & Burgess, "Internalisation and Recycling of the Granulocyte–Macrophage Colony–Stimulating Factor (GM–CSF) Receptor on a Murine Myelomonocytic Leukemia", *J. Cell. Phys.* 130:255–261 (1987).

Wharton et al., "Membrane Fusion by Peptide Analogues of Influenza Virus Haemagglutinin", *J. gen. Virol.* 69:1847–1857 (1988).

Wienhues et al., "A novel method for transfection and expression of reconstituted DNA–protein complexes in eukaryotic cells", *DNA* 6:81–89 (1987).

Wilchek & Bayer, "The Avidin–Biotin Complex in Bioanalytical Applications", *Analyt. Biochem.* 171:1–32 (1988).

Willumsen et al., "Intracellular Cl⁻ activity and cellular Cl⁻ pathways in cultured human pathway epithelium", *Am. J. Physiol.* 256:C1033–C1034 (1989).

Wilson et al., "A Novel Mechanism for Achieving Transgene Persistence in Vivo after Somatic Gene Transfer into Hepatocytes", *J. Biol. Chem.* 267:11483–11489 (Jun. 5, 1992).

Wood et al., "Expression of active human factor VIII from recombinant DNA clones", *Nature* 312:330–337 (Nov. 22, 1984).

Wu & Wu, "Receptor–mediated in Vitro Gene Transformation by a Soluble DNA Carrier System", *J. Biol. Chem.* 262:4429–4432 (Apr. 5, 1987). Wu & Wu, "Evidence for Targeted Gene Delivery to Hep G2 Hepatoma Cells in Vitro", *Biochemistry 27:887–892 (1988).*

Wu & Wu, "Receptor–mediated Gene Delivery and Expression in Vivo", *J. Biol. Chem.* 263:14621–14624 (Oct. 15, 1988), Yankaskas et al., "E6 and E7 Genes of Human Papilloma Virus 18 (HPV 18) Transform Human Airway Epithelial Cells", *Genetics and Epithelial Cell Dysfunctions in Cystic Fibrosis,* Alan R. Liss, Inc. A139 (1991).

Zamecnik et al., "Inhibition of replication and expression of human T–cell hymphotropic virus type III in cultured cells by exogenous synthetic oligonucleotides complementary to viral RNA", *Proc. Natl. Acad. Sci. USA* 83:4143–4146 (Jun. 1986).

Zatloukal et al., "Hepatocellular Cytokeratins as Substrates of Transglutaminases", *Lab. Investig.* 61:603–608 (1989).

Zatloukal et al., "Transferrininfection: receptor–mediated gene delivery in vitro and in vivo", *Cold Spring Harbor Gene Therapy Conference",* (Jul. 1992).

Zhang & Nagaraja, "Differentiation of avian adenovirus type–II strains by restriction endonuclease fingerprinting", *Am. J. Vet. Res. 50:1466–1470 (Sep. 1989).*

Berkner Biotechniques 616–689, 1989.

Hirsch et al C89–126505 (Derwent Abs) 1989.

Wu et al. Biochemistry 27 887–892 1988.

Zenke et al. PNAS 87:2655–3659 1990 May.

Persson et al. Journal of Virology 46:956–963 1983.

Harris et al. TibTech vol. (11) 1993 p. 42.

Osband et al. Immunology today vol. 11 No. 6 1990 p. 193.

SITE I:       -160-GCT-GAG-CAG-CAA-165-
                              ↓ MUTAGENESIS
                     | GAT ATC |   Eco RV

SITE II:  -187-GTC-GAA-GGT-CAA-ACA-CCT-AAA-195-
                              ↓ MUTAGENESIS
                     | CAC GTG |   Pml I

SITE III:   -268-TCA-ACT-ACT-GAG-GCG-ACC-GCA-
                GGC-AAT-GGT-GAT-AAC-TTG-ACT-282-
                              ↓ MUTAGENESIS
                     | AGT ACT |   Sca I

SITE IV:    -425-CTT-ACC-AAG-GTA-AAA-CCT-AAA-
                 ACA-GGT-CAG-GAA-AAT-GGA-439-
                              ↓ MUTAGENESIS
                     | GAT ATC |   Eco RV

CONJUGATES FOR INTRODUCING NUCLEIC ACID INTO HIGHER EUCARYOTIC CELLS

The present invention was made with U.S. Government support. The U.S. Government has certain rights in the invention.

CROSS REFERENCE TO RELATED APPLICATIONS

This application is a continuation of application Ser. No. 07/949,205, filed Sep. 23, 1992 now abandoned, which is a CIP of application Ser. No. 07/864,758 filed Apr. 7, 1992 now abandoned, which is a CIP of application Ser. No. 07/827,049 filed Jan. 30, 1992 now abandoned, which is a CIP of application Ser. No. 07/767,787 filed Sep. 30, 1991 now abandoned.

FIELD OF THE INVENTION

The invention is in the field of DNA technology. In particular, the invention relates to the introduction of nucleic acids into higher eucaryotic cells.

BACKGROUND OF THE INVENTION

There is a need for an efficient system for introducing nucleic acid into live cells particularly in gene therapy. Genes are introduced into cells in order to achieve in vivo synthesis of therapeutically effective genetic products, e.g. in order to replace the defective gene in the case of a genetic defect. "Conventional" gene therapy is based on the principle of achieving a lasting cure by a single treatment. However, there is also a need for methods of treatment in which the therapeutically effective DNA (or mRNA) is administered like a drug ("gene therapeutic agent") once or repeatedly as necessary. Examples of genetically caused diseases in which gene therapy represents a promising approach are hemophilia, beta-thalassaemia and "Severe Combined Immune Deficiency" (SCID), a syndrome caused by the genetically induced absence of the enzyme adenosine deaminase. Other possible applications are in immune regulation, in which humoral or intracellular immunity is achieved by the administration of functional nucleic acid which codes for a secreted protein antigen or for a non-secreted protein antigen, by immunization. Other examples of genetic defects in which a nucleic acid which codes for the defective gene can be administered, e.g. in a form individually tailored to the particular requirement, include muscular dystrophy (dystrophin gene), cystic fibrosis (cystic fibrosis transmembrane conductance regulator gene), hypercholesterolemia (LDL receptor gene). Gene-therapy methods of treatment are also potentially of use when hormones, growth factors or proteins with a cytotoxic or immune-modulating activity are to be synthesized in the body.

Gene therapy also appears promising for the treatment of cancer by administering so-called "cancer vaccines." In order to increase the immunogenicity of tumor cells, they are altered to render them either more antigenic or to make them produce certain cytokines in order to trigger an immune response. This is accomplished by transfecting the cells with DNA coding for a cytokine, e.g. IL-2, IL-4, IFN gamma, or TNF alpha. To date, gene transfer into autologous tumor cells has been accomplished via retroviral vectors.

The mode of activity of antisense RNAs and DNAs as well as ribozymes enables them to be used as therapeutic agents for blocking the expression of certain genes (such as deregulated oncogenes or vital genes) in vivo. It has already been shown that short antisense oligonucleotides can be imported into cells and exert their inhibiting effect therein (Zamecnik et al., 1986), even if their intracellular concentration is low, caused, inter alia, by their restricted uptake by the cell membrane as a result of the strong negative charge of the nucleic acids. The oligonucleotides may be modified, e.g. by substituting the charged phosphodiester groups by uncharged groups. Another possible method of direct modification consists in using nucleoside analogues.

Various techniques are known for gene transfer into mammalian cells in vitro but their use in vivo is limited (these include the introduction of DNA by means of liposomes, electroporation, microinjection, cell fusion, DEAE-dextran or the calcium phosphate precipitation method).

In recent times, biological vectors have been developed to bring about the transfer of genes by using the efficient entry mechanisms of their parent viruses. This strategy was used in the construction of recombinant retroviral and adenoviral vectors in order to achieve a highly efficient gene transfer in vitro and in vivo (Berkner, 1988). For all their efficiency, these vectors are subject to restrictions in terms of the size and construction of the DNA which is transferred. Furthermore, these agents constitute safety risks in view of the co-transfer of viable viral gene elements of the original virus. Thus, for example, the use of retroviruses is problematic because it involves, at least to a small percentage, the danger of side effects such as infection with the virus (by recombination with endogenous viruses and possible subsequent mutation into the pathogenic form) or the formation of cancer. Moreover, the stable transformation of the somatic cells of the patient, as achieved by means of retroviruses, is not desirable in each case because this can only make the treatment more difficult to reverse, e.g. if side effects occur.

In order to circumvent these restrictions, alternative strategies for gene transfer have been developed, based on mechanisms which the cell uses for the transfer of macromolecules. One example of this is the transfer of genes into the cell via the extremely efficient route of receptor-mediated endocytosis (Wu and Wu, 1987, Wagner et al., 1990 and EP-A1 0388 758). This approach uses bifunctional molecular conjugates which have a DNA binding domain and a domain with specificity for a cell surface receptor (Wu and Wu, 1987, Wagner et al., 1990). If the recognition domain (hereinafter referred to as the "internalizing factor") is recognized by the cell surface receptor, the conjugate is internalized by the route of receptor-mediated endocytosis, in which the DNA bound to the conjugate is also transferred. Using this method, it was possible to achieve gene transfer rates at least as good as those achieved with the conventional methods (Zenke et al., 1990).

Whereas this vector system is able to transport large quantities of DNA into cells having the suitable cell surface receptor, the corresponding gene expression very often does not accord with the transfer capacity (Cotten et al., 1990). It was assumed, inter alia, that the reason for this phenomenon is that the DNA conveyed into the cell by receptor-mediated endocytosis lands in lysosomes where it undergoes degradation (Zenke et al., 1990, Cotten et al., 1990). Therefore, the fact that the DNA internalized in lysosomes does not have any specific mechanism for leaving the intracellular vesicle system constitutes a restriction which is inherent in this transport system.

The aim of the present invention was to reduce or eliminate these restrictions.

A plurality of viruses effect their entry into the eucaryotic host by means of mechanisms which correspond in principle to the mechanism of receptor-mediated endocytosis. Virus infection based on this mechanism generally begins with the binding of virus particles to receptors on the cell membrane. After this, the virus is internalized into the cell. This internalizing process follows a common route, corresponding to the entrance of physiological ligands or macromolecules into the cell: first of all, the receptors on the cell surface arrange themselves in groups, and the membrane is inverted inwardly and forms a vesicle surrounded by a coating. After this vesicle has rid itself of its clathrin coat, acidification takes place inside it by means of a proton pump located in the membrane. This triggers the release of the virus from the endosome. Depending on whether the virus has a lipid coat or not, two types of virus release from the endosome were taken into account: in the case of so-called "naked" viruses (e.g. adenovirus, poliovirus, rhinovirus) it was suggested that the low pH causes changes in configuration in virus proteins. This exposes hydrophobic domains which are not accessible at the physiological pH. These domains thus acquire the ability to interact with the endosome membrane and thereby cause the release of the virus genome from the endosome into the cytoplasm. As for viruses with a coat (e.g. vesicular stomatitis virus, Semliki Forest virus, influenza virus) it is presumed that the low pH modifies the structure or configuration of some virus proteins, thereby promoting the fusion of the virus membrane with the endosome membrane. Viruses which penetrate into the cell by means of this mechanism have certain molecular peculiarities which enable them to break up the endosome membrane in order to gain entry into the cytoplasm.

Other viruses, e.g. the coated viruses Sendai, HIV and some strains of Moloney leukaemia virus, or the uncoated viruses SV40 and polyoma, do not need a low pH for penetration into the cell; they can either bring about fusion with the membrane directly on the surface of the cell (Sendai virus, possibly HIV) or they are capable of triggering mechanisms for breaking up the cell membrane or passing through it. It is assumed that the viruses which are independent of pH are also capable of using the endocytosis route (McClure et al., 1990).

In experiments which preceded the present invention it was established that gene transfer by means of nucleic acid complexes in which the nucleic acid is complexed with polycations, optionally coupled to an internalizing factor, e.g. with transferrin-polylysine conjugates, is significantly increased by treatment with adenoviruses, specific retroviruses or with virus fragments. This effect was achieved by making use of the phenomenon that these viruses are taken up into the cells by endocytosis mechanisms and have a specific mechanism for escaping from the vesicle system by breaking open the endosomes, e.g. in the case of the adenoviruses (Pastan et al., 1986).

Starting from these observations, the problem of the invention was solved by developing a bioconjugate which contains the virus as an integral part of its functional construct.

SUMMARY OF THE INVENTION

The invention relates to new conjugates which have the ability to form complexes with nucleic acid and which comprise an internalizing factor and a substance having an affinity for nucleic acid, for introducing nucleic acid into higher eucaryotic cells, characterized in that the internalizing factor may be a virus which is bound to the substance having an affinity for nucleic acid via an antibody in such a way that it is capable per se of penetrating into the cell as part of the conjugate/nucleic acid complex and of releasing the contents of the endosomes, in which the complex is located after entering the cell, into the cytoplasm.

The invention also relates to complexes comprising a nucleic acid and a conjugate of the invention comprising an internalizing factor and a substance having an affinity for nucleic acid.

The invention further relates to complexes useful for transforming higher eucaryotic cells which have few or no viral receptors characterized in that they further comprise a second conjugate of an internalizing factor bound to a substance having an affinity for nucleic acid, wherein the internalizing factor is specific for a surface receptor of the higher eucaryotic cell, and wherein the virus conjugate and the internalizing factor conjugate are complexed with the nucleic acid.

The invention also relates to a process for introducing nucleic acid into higher eucaryotic cells, characterized in that the cells are treated with one of the nucleic acid complexes of the invention as described herein.

The invention also relates to pharmaceutical compositions, characterized in that they comprise as an active component one of the nucleic acid complexes of the invention.

DESCRIPTION OF THE FIGURES

FIG. 7A. Relative levels of gene expression mediated by human transferrin-polylysine-DNA complexes, adenovirus-polylysine-DNA complexes, and ternary complexes containing a combination of adenovirus and human transferrin domains. Transferrin-polylysine-DNA complexes were formed by combination of pRSVL DNA (6 µg) with human transferrin-polylysine conjugate (12 µg) as described (Wagner et al., 1990) [hTfpL]. Adenovirus-polylysine-DNA complexes [AdpL] were prepared as in FIG. 3. Chimeric complexes were formed by sequential addition of polylysine monoclonal antibody MP301pLys (2 µg), plasmid DNA pRSVL (6 µg), and human transferrin-polylysine (9 µg) to the epitope-tagged adenovirus P202-Ad5 ($2.5\times10^{10}$ particles) [AdpL/hTfpL]. Delivery to HeLa cells and evaluation of reporter gene expression was as before. FIG. 7B. Relative susceptibility to gene transfer by adenovirus-human transferrin ternary complexes. Chimeric complexes containing a combination of adenovirus and human transferrin domains were formed as above. Delivery to the cell lines HeLa and HBE1 and analysis of reporter gene expression was as for FIG. 3.

FIG. 12A. Example of bronchus of cotton rats treated with hTfpL/AdpL complexes containing plasmid DNA pRc/RSV; FIG. 12B. Example of bronchus of cotton rats treated with hTfpL/AdpL complexes containing plasmid DNA pCMVβ; FIG. 12C. Example of distal airway region of cotton rats treated with hTfpL/AdpL complexes containing plasmid DNA pRc/RSV; FIG. 12D. Example of distal airway region of cotton rat treated with hTfpL/AdpL complexes containing plasmid DNA pCMVβ. Magnification 600×. FIG. 12E. Enlargement of β-galactosidase positive region from lungs of cotton rat treated with hTfpL/AdpL complexes containing plasmid DNA pCMVβ. Magnification 1000×.

DESCRIPTION OF THE PREFERRED EMBODIMENTS

Figure 1:
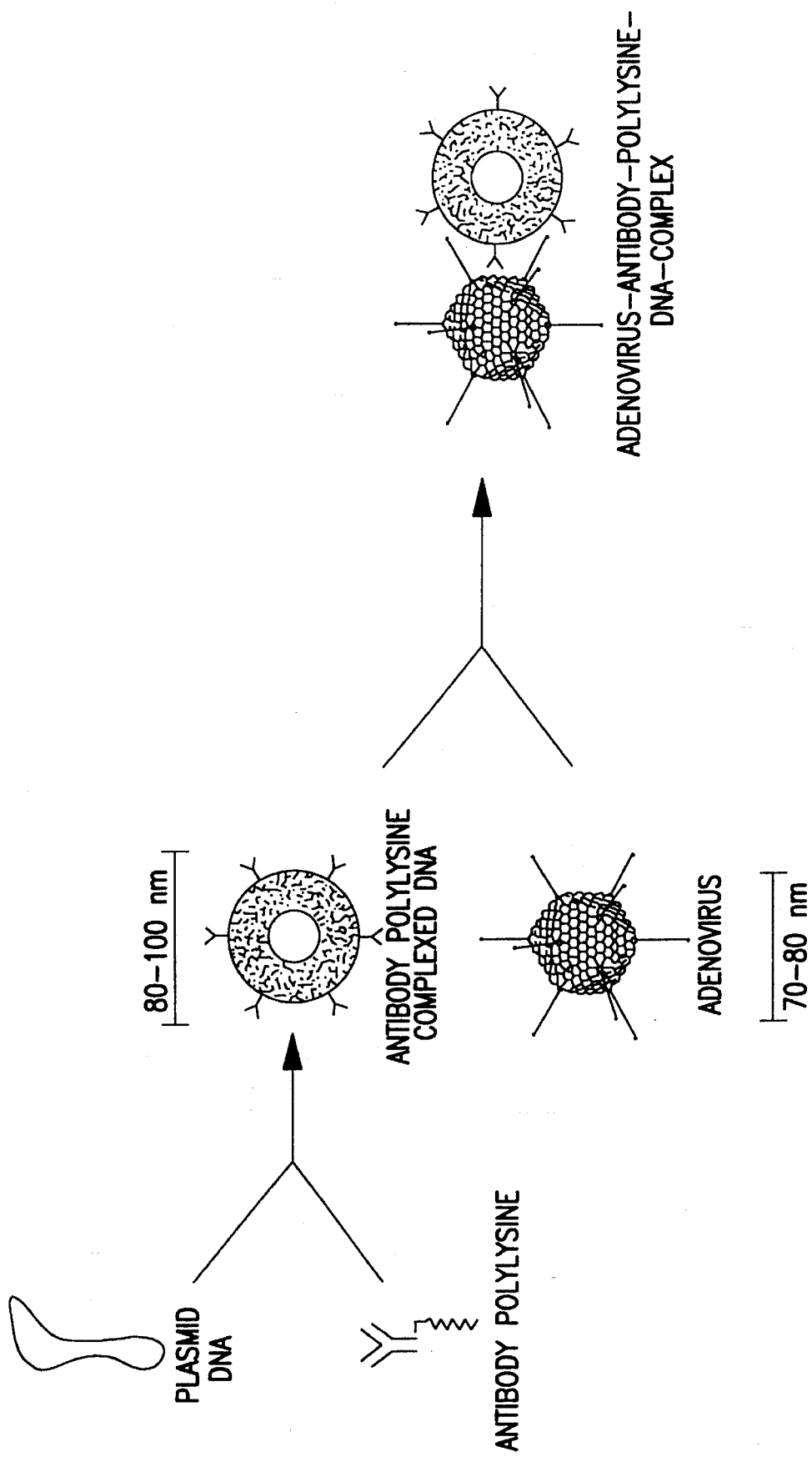
FIG. 1: Diagrammatic representation of adenovirus-polycation-DNA complexes containing a foreign epitope on the adenovirus capsid. To accomplish linkage of an adenovirus and a polycationic DNA-binding domain, the chimeric adenovirus P202-Ad5 containing a heterologous epitope in the exterior domain of its hexon protein was employed in conjunction with the monoclonal antibody MP301 specific for this epitope. The monoclonal antibody was rendered competent to carry foreign DNA sequences by attaching a polylysine moiety. Interaction of the polylysine-antibody complexed DNA with adenovirus P202-Ad5 occurs via the specificity of the conjugated antibody.

The present invention thus relates to a conjugate which has the ability to form complexes with nucleic acid and which consists of an internalizing factor and a substance having an affinity for nucleic acid, for introducing nucleic acids into higher eucaryotic cells. The conjugate is characterized in that the internalizing factor is a virus which is bound to the nucleic acid-binding substance via an antibody in such a way as to be capable per se of penetrating into the cell as part of the conjugate/nucleic acid complex and of releasing the content of the endosomes, in which the complex is located after entering the cell, into the cytoplasm. Such conjugates are useful for introducing nucleic acid into higher eucaryotic cells which have adenoviral receptors. The invention further relates to complexes useful for transforming higher eucaryotic cells which have few or no viral receptors characterized in that they further comprise a second conjugate of an internalizing factor bound to a substance having an affinity for nucleic acid, wherein the internalizing factor is specific for a surface receptor of the higher eucaryotic cell, and wherein the virus conjugate and the internalizing factor conjugate are complexed with the nucleic acid.

The ability of the virus to penetrate into the cell and release the content of the endosomes, in which the conjugate/nucleic acid complex is located, into the cytoplasm, is hereinafter referred to as the "up-take function".

The conjugates according to the invention combine the advantages of vector systems based on internalizing factor conjugates with the advantages which the viruses bring into these systems.

Compared with gene transfer by receptor-mediated endocytosis, the virus-polycation-DNA complexes according to the invention have the advantage that they circumvent the fundamental restriction inherent in the known molecular conjugate systems, in that, unlike the known conjugates, they have a specific mechanism which enables them to be released from the cell vesicle system. Compared with biological vectors, the vector system according to the invention constitutes a fundamental conceptual departure from the recombinant viral vectors, in that the foreign DNA which is to be transported is carried on the outside of the virion. Consequently, the conjugates according to the invention can transport very large gene constructs into the cell, with no restrictions of any kind as to the sequence.

The suitability of a virus within the scope of the present invention is defined by its uptake function. Suitable viruses include, on the one hand, those which are able to penetrate into the cell by receptor-mediated endocytosis and to bring about their release—and hence the release of the nucleic acid—from the endosome into the cytoplasm. (The suitability of viruses within the scope of the present invention is further defined in that they retain this property even when they are a component of the nucleic acid complexes).

Without wishing to be tied to this theory, this mechanism could benefit the nucleic acid complexes transferred into the cell in so far as the ability of the virus to release the contents of the endosomes prevents the fusion between the endosomes and lysosomes and consequently prevents the enzymatic decomposition which normally occurs in these cell organelles.

The higher eucaryotic cells are well known and do not include yeast. See *Molecular Biology of the Gene*, James D. Watson et al., the Benjamin/Cummings Publishing Company, Inc., pp. 676–677 (1987). For examples of higher eucaryotic cells capable of adenovirus infection, reference in made to Fields, B. N. and Knipe, D. M. (1990).

The susceptibility of a given cell line to transformation by a virus as a facilitator/ligand of conjugate entry is dependent upon the presence and number of target cell surface receptors for the virus. Methods for determining the adenoviral cell surface receptor number for HeLa and KB cells are taught by Svensson, 1985, and Defer, 1990. It is thought that the receptor for the adenovirus is rather ubiquitously expressed. Thus, many cell lines are transformable by a vector system comprising an adenovirus or part thereof. However, some higher eucaryotic cells have few or no viral receptors. When transforming such cells, it may be necessary to employ a second conjugate of an internalizing factor bound to a substance having an affinity for nucleic acid, wherein the internalizing factor is specific for a surface receptor of the higher eucaryotic cell, and wherein the virus conjugate and the internalizing factor conjugate are complexed with the nucleic acid. Such "ternary complexes" may be used successfully to augment the transformation of higher eucaryotic cells such as the respiratory epithelial cell line HBE1 which has a relatively low cell surface population of adenoviral receptors.

Viruses whose uptake function, occurring at the start of infection, occurs by receptor-mediated endocytosis and which are suitable as part of the conjugates according to the invention by virtue of this property, include on the one hand viruses without a lipid coat such as adenovirus, poliovirus, rhinovirus, and on the other hand the enveloped viruses vesicular stomatitis virus, Semliki Forest virus, influenza virus; pH-dependent strains of Moloney virus are also suitable. Preferably, the virus is adenovirus subgroup C, type 5, Semilki Forest Virus, Vesicular Stomatitits Virus, Poliovirus, Rhinoviruses and Moloney Leukemia Virus. While the entry cycles of many viruses have not been completely characterized, it is likely that many other viruses will exhibit the required uptake function and, thus, will be useful in the methods of the invention.

An important advantage derived from the present invention is that the foreign DNA to be transferred is not integrated into the genome of the parent virus, as in the case with standard recombinant viral vectors (see Berkner, 1988; Eglitis and Anderson, 1988). Thus, the present invention provides much greater flexibility as to the design of the foreign gene sequence to be expressed, as transcription is not dependent on promoters in the parent virus gene. In addition, this strategy allows a greatly increased size of foreign DNA that can be transferred, as the packaging constraints of the virus do not limit the amount of DNA that can be carried on the exterior. Over and above these practical and immediate advantages, important potential safety features derive from the design of the vector. Conventional recombinant vital vectors mediate obligatory co-delivery of genome elements of the parent virus from which potential safety hazards derive (Ledley, 1989; Anderson, 1984). Since the adenovirus-polylysine complexes selectively exploit viral entry features, the viral genome is not an essential feature. This design allows the possibility of modifying the present system with a functionally and/or structurally inactivated viral genome to minimize the safety hazards deriving from the transfer of viable genes from the parent virus.

Within the scope of the present invention, the term viruses—provided that they have uptake function as defined above—includes in addition to the wild types, mutants which have lost certain functions of the wild type, other than their uptake function, especially their ability to replicate, as a result of one or more mutations. However, mutants which have lost their uptake function can be employed in the practice of the invention so long as they are employed as part of a "ternary complex" as defined herein and the mutant virus has not lost its endosomolysis activity.

Mutants may be produced by conventional mutagenesis processes by mutations in virus-protein regions which are responsible for the replicative functions and which may be complemented by a packaging line. These include, e.g. in the case of adenovirus, ts-mutants (temperature sensitive mutants), E1A- and E1B-mutants, mutants which exhibit mutations in MLP-driven genes (Berkner, 1988) and mutants which exhibit mutations in the regions of certain capsid proteins. Virus strains which have corresponding natural mutations are also suitable. The ability of viruses to replicate can be investigated, for example, using plaque assays known from the literature, in which cell cultures are covered with suspensions of various virus concentrations and the number of lysed cells which is visible by means of plaques is recorded (Dulbecco, 1980).

Other viruses which may be suitable for use within the scope of the invention include so-called defective viruses, i.e. viruses which, in one or more genes, lack the function necessary for autonomous virus replication, for which they require helper viruses. Examples of this category are DI-particles (defective interfering particles) which are derived from the infectious standard virus, have the same structural proteins as the standard virus, have mutations and require the standard virus as a helper virus for replication (Huang, 1987; Holland, 1990). Examples of this group also include the satellite viruses (Holland, 1990). Another group is the class of parvoviruses called the adeno-associated virus (Berns, K. I., 1990).

Also suitable within the scope of this invention may be attenuated live vaccines (Ginsberg, 1980) or vaccination strains.

The term viruses within the scope of the present invention also includes inactivated viruses, e.g. viruses inactivated by chemical treatment such as treatment with formaldehyde, by UV-radiation, by chemical treatment combined with UV-radiation, e.g. psoralen/UV-radiation, by gamma-radiation or by neutron bombardment, as well as parts of viruses, e.g. the protein content freed from nucleic acid (the empty virus capsid), provided that they have the uptake functions of the intact virus.

Inactivated viruses that are also used for vaccines, for example, may be prepared by standard methods known from the literature (Davis and Dulbecco, 1980, Hearst and Thiry, 1977) and then tested to see whether they are suitable as components of the conjugates according to the invention.

The virus may possibly be a chimeric virus which has a foreign epitope in a region which is not essential for the uptake function. However, even when such chimeric viruses have lost their uptake function, they may be employed according to the invention as part of a "ternary complex" as defined herein, so long as the virus has not lost its endosomolysis properties.

In order to select a virus, an inactivated virus or a virus component for the particular transfection which is to be carried out, the process used may be, for example, to investigate the virus first of all in preliminary tests to see whether it has an effect when the nucleic acid/polycation complexes are taken up into the target cell. Furthermore, its uptake functions may be tested by using it in transfection with bioconjugates, e.g. transferrin-polycation conjugates or another bioconjugate with specificity for the target cell to be transfected, and checking its ability to increase the gene transfer capacity by measuring the expression of a reporter gene.

When intact viruses are used, tests are carried out, preferably in parallel to the preliminary tests investigating the virus for its ability to augment gene transfer, with or without a second conjugate comprising an internalizing factor linked to a substance having an affinity for a nucleic acid, to see whether the virus is capable of replicating. The investigation for ability to replicate is carried out using plaque assays (see above) in the case of cytopathic viruses or in the case of viruses which significantly impair the growth of the host cells. For other viruses, detection methods specific to the virus in question are used, e.g. the hemagglutination test or chemico-physical methods (using an electron microscope).

Within the scope of this invention, the preferred viruses are those which can be produced in a high titre, which are stable, have low pathogenicity in their native state and in which a targeted elimination of the ability to replicate is possible, especially adenoviruses. If a specific cell population is to be transfected, viruses which specifically infect this cell population are preferred. If the transfection is intended to attack different cell types, viruses which are infectious for a wide range of cell types are used.

In any case, for therapeutic use of the invention in vivo, only those viruses or virus components may be used in which the safety risks are minimized as far as possible, particularly the risk of replication of the virus in the cell and recombination of virus DNA with host DNA.

In preliminary tests, adenovirus preparations were inactivated using a conventional UV sterilizing lamp or with formaldehyde and it was found, surprisingly, that the extent of inactivation of the viruses was substantially greater than the reduction in the gene transfer effect. This is a clear indication that mechanisms connected with the normal infection mechanism in the active virus can be destroyed without eliminating the effect which is essential for gene transfer.

Substances with an affinity for nucleic acid which may be used according to the invention include, for example, homologous polycations such as polylysine, polyarginine, polyornithine or heterologous polycations having two or more different positively charged amino acids, these polycations possibly having different chain lengths, and also non-peptidic synthetic polycations such as polyethyleneimine. Other substances with an affinity for nucleic acid which are suitable are natural DNA-binding proteins of a polycationic nature such as histones or protamines or analogues or fragments thereof.

The complexes according to the invention may optionally contain, in addition to the virus conjugate, another conjugate in which a substance having an affinity for nucleic acid, generally the same one as in the virus conjugate, is coupled with an internalizing factor having an affinity for the target cell. This embodiment of the invention is used particularly when the target cell has no or few receptors for the virus. In the presence of another internalizing factor-binding factor conjugate, the virus profits from the internalizing ability of the second conjugate, by being complexed to the nucleic acid together with the second conjugate and being taken up into the cell as part of the resulting "combi-complex".

Specifically, preliminary tests can determine whether the use of another internalizing factor permits or improves the uptake of nucleic acid complexes, by carrying out parallel transfections with nucleic acid complexes, first without any additional internalizing factor, i.e. with complexes consisting of nucleic acid and virus conjugate, and on the other hand with complexes in which the nucleic acid is conjugated with another conjugate consisting of an additional internalizing factor for which the target cells have a receptor, and a substance having an affinity for nucleic acid.

If an additional internalizing factor is used, it is defined particularly by the target cells, e.g. by specific surface antigens or receptors specific to a cell type which thus permit the targeted transfer of nucleic acid into this type of cell.

The term "internalizing factor" for the purposes of the present invention refers to ligands or fragments thereof which, after binding to the cell are internalized by endocytosis, preferably receptor-mediated endocytosis, or factors the binding or internalizing of which is carried out by fusion with elements of the cell membrane.

Suitable internalizing factors include the ligands transferrin (Klausner, R. D. et al., 1983), conalbumin (Sennett, C. et al., 1981), asialoglycoproteins (such as asialotransferrin, asialorosomucoid or asialofetuin) (Ashwell, G. et al., 1982), or substances which contain galactose and are internalized by the asialoglycoprotein receptor, mannosylated glycoproteins (Stahl, P. D. et al., 1987), lysosomal enzymes (Sly, W. et al., 1982), LDL (Goldstein, J. L. et al., 1982), modified LDL (Goldstein, J. L. et al., 1979), lipoproteins which are taken up into the cells via receptors (apo B100/LDL); viral proteins such as the HIV protein gp120; antibodies (Mellman, I. S. et al., 1984; Kuhn, L. C. et al., 1982), Abrahamson, D. R. et al., 1982), or fragments thereof against cell surface antigens, e.g. anti-CD4, anti-CD7; cytokines such as interleukin-1 (Mizel, S. B. et al., 1987), Interleukin 2 (Smith, K. A. et al., 1985), TNF (Imamure, K. et al., 1987), interferon (Anderson, P. et al., 1982), colony-stimulating factor (Walker, F. et al., 1987); factors and growth factors such as insulin (Marshall, S., 1985), EGF (Carpenter, G., 1984), platelet-derived growth factor (Heldin, C.-H. et al., 1982), transforming growth factor β (Massague, J. et al., 1986), nerve growth factor (Hosang, M. et al., 1987), insulin-like growth factor I (Schalch, D. S. et al., 1986), LH, FSH, (Ascoli, M. et al., 1978), growth hormone (Hizuka, N. et al., 1981), prolactin (Posner, B. I. et al., 1982), glucagon (Asada-Kubota, M. et al., 1983), thyroid hormones (Cheng, S.-Y. et al., 1980); α-2-macroglobulin protease (Kaplan, J. et al., 1979); and "disarmed" toxins. The ligands may be of natural or synthetic origin. See, *Trends Pharmacol. Sci.* 10:458–462 (1989), and the references cited therein.

The following are essential requirements for the suitability of such factors according to the present invention, a) that they can be internalized by the specific cell type into which the nucleic acid is to be introduced and their ability to be internalized is not affected or only slightly affected if they are conjugated with the binding factor, and b) that, within the scope of this property, they are capable of carrying nucleic acid "piggyback" into the cell by the route they use.

Without being pinned down to this theory, the combi-complexes are taken up by cells either by binding to the surface receptor which is specific to the internalizing factor or by binding to the virus receptor or by binding to both receptors by receptor-mediated endocytosis. When the virus is released from the endosomes, the DNA complexed to the viruses is also released into the cytoplasm and thereby escapes the lysosomal degradation.

The binding of the virus to the substance having an affinity for nucleic acid results in the following advantages:

1) Wider applicability of the gene transfer technology with nucleic acid complexes, since the viruses themselves may constitute the internalizing factor or may also be complexed to the DNA in conjunction with another internalizing factor (e.g. transferrin or asialofetuin etc.). In this way it is possible to make use of the positive effect of the viruses even for cells which do not have any receptor for the virus in question.

2) Improvement in the efficiency of gene transfer, since the binding of the viruses to the DNA ensures that they are jointly taken up into the cells. The coordinated uptake and release of viruses and DNA also gives rise to the possibility of a reduction in the quantity of DNA and viruses required for efficient gene transfer, which is of particular importance for use in vivo.

In the experiments carried out according to the invention, human transferrin was used as an additional internalizing factor; moreover, the performance of the conjugates according to the invention was demonstrated by means of complexes of DNA and polylysine-conjugated virus which contained no additional internalizing factor-binding factor conjugate.

The binding of the virus to the substance having an affinity for nucleic acid is achieved by covalent bonding of the substance with an affinity for nucleic acid to an antibody. It is preferable to use an antibody which binds to an epitope in a virus protein region not involved in the uptake function of the virus.

In the tests carried out within the scope of the invention, the binding between an adenovirus and a polycation was achieved by covalently conjugating an antibody with specificity for the adenovirus capsid to a polylysine molecule. It is known that the adenovirus fibre and pentone proteins are essential for the binding of the virus and its uptake into the cell, whereas the main capsid protein hexon is of lesser importance in these processes. Therefore, an antibody was used which brings about the binding of the adenovirus to polylysine by recognition of an epitope on the hexon protein. Non-neutralizing anti-hexon monoclonal antibodies are taught by Russell, W. C. et al. (1981). This specific binding may also be achieved by using, on the one hand, a chimeric adenovirus which has a foreign epitope in the surface region of its hexon protein. On the other hand, a monoclonal antibody was used which is specific for the heterologous epitope. (This construction is diagrammatically shown in FIG. 1). This results in a binding of the adenovirus to polylysine without functionally destroying the capsid proteins.

The use of a special antibody for establishing the bond between the virus and the nucleic acid-binding substance is not critical. The prerequisite for the suitability of a particular antibody is that it should not neutralize, or should only partly neutralize, the uptake function of the virus.

Within the scope of the present invention, antibodies against epitopes in virus protein regions which are not essential for the uptake function are preferred. Examples of such virus regions are the hexon protein of the adenovirus mentioned above or influenza neuraminidase.

However, antibodies with specificity for virus proteins which are involved in the uptake function are also suitable, provided that it is ensured, by maintaining a suitable stoichiometric ratio, that the antibody occupies only part of the cell binding regions of the virus, so that them are still sufficient domains free for the binding of the virus to the cell. Alternatively, antibodies which block the uptake function of the virus may be used so long as the complex further comprises a second conjugate comprising an internalizing factor linked to a substance having affinity for nucleic acid (the "ternary complexes"). The quantity of antibody suitable for the specific application can be determined by titration.

Monoclonal antibodies, possibly the Fab' fragments thereof, are preferred.

Figure 8A:
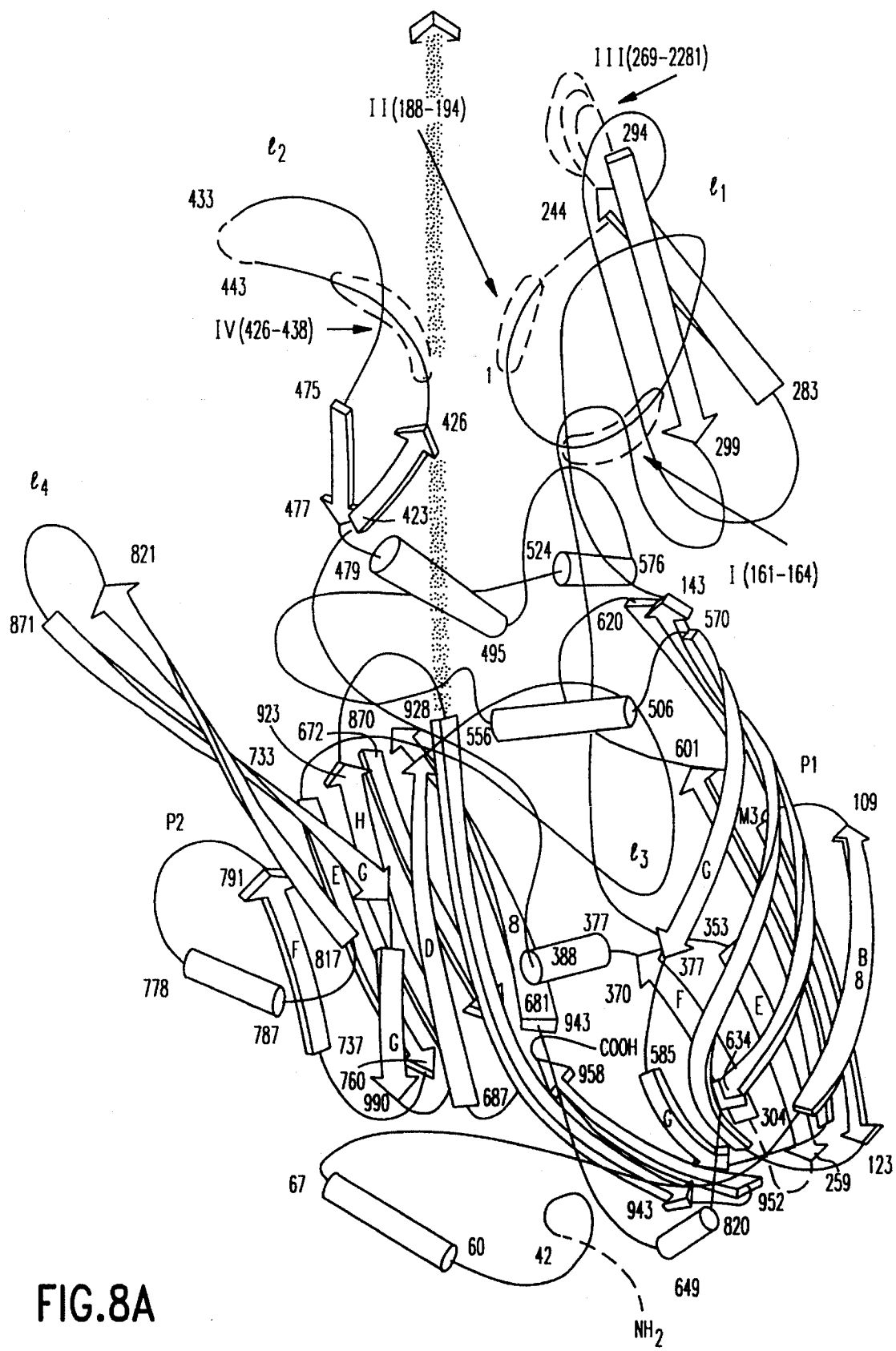
FIG. 8 Potential insertion sites created in the Ad5 hexon gene sequence by site-directed mutagenesis. In vitro mutagenesis was performed using the plasmid EcoRIAd5 which contains the left half (0–76 m.u.) of the Ad5 genome. The hexon gene is located between m.u. 52–60. The three-dimensional sketch of the hexon subunit is adapted from Roberts et al., 1986.

If the virus is a chimeric virus with a foreign epitope, the antibody is directed against this epitope. Preferably, the virus is a chimeric adenovirus where the coding sequence for the hexon region has been modified to include a sequence coding for a heterologous protein for which an antibody can be raised. The hexon protein is composed of a highly conserved base domain and three less conserved loops that are highly exposed on the surface of the viron (Roberts et al., 1986). There are several short regions in these loops where the Ad2 and Ad5 amino acid sequences are dissimilar, with Ad5 showing changes as well as deletions compared to Ad2. These are potential sites for the insertion of the heterologous gene sequences coding for the heterologous protein which may be used to immunologically link the adenovirus to the substance having affinity for the nucleic acid. Preferably, the heterologous gene sequence is inserted in the Ad5 gene sequence at amino acid positions 161–165, 188–194, 269–281 and 436–438, referred to as sites I, II, III and IV, respectively (see FIG. 8). At each potential site, a unique restriction site may be created by means of site-directed mutagenesis of a subclone of the Ad5 hexon gene. Nucleotides coding for nonconserved amino acids may be deleted at the same time, leaving more space for insertion of the heterologous gene sequence. In general, because of the small numbers of amino acids which can be inserted at sites I, II, III and IV (up to about 65 amino acids), the heterologous gene sequence codes for only the amino acid corresponding to the epitope and a minimal number of flanking sequences.

The epitope specificity of a particular monoclonal antibody to a heterologous protein may be determined by peptide scanning. See Geysen, et al., 1984, 1985, 1986, 1986; and European Patent Application Publication No. 392,369 (1990), the disclosures of which are fully incorporated by reference herein. According to this method, overlapping 8-amino acid long peptides of the heterologous protein are prepared by methods of solid phase synthesis. For example, peptide 1 consists of amino acids 1–8, peptide 2 of amino acids 2–9, and so on. The peptides remain bound to the solid carrier after synthesis. Hybridoma cell culture supernatants or purified monoclonal antibodies thereof are then tested for reactivity to the immobilized peptides by ELISA. Once the epitopic region is identified, the gene sequence coding for the epitopic region may then be inserted into any one of the restriction sites of regions I, II, III or IV.

There are many examples of proteins and antibodies which are specific for the protein. One of ordinary skill in the art can select a heterologous protein-antibody combination which is operable in the present invention with no more than routine experimentation. For example, the known coding sequence for a protein, for which an antibody thereto is also known, may be inserted into the hexon region of an adenovirus. The resulting chimeric virus can then be tested for immunological binding, for example, to labeled antibody in a competition, ELISA or other immunoassay format. Such immunoassay techniques are well known and are practiced routinely by those of ordinary skill in the art.

The antibody-polycation conjugates can be produced chemically by a method known per se for the coupling of peptides, preferably using the method described by Wagner et al., 1990, and in EP-A1 388 758.

If monoclonal antibodies have suitable carbohydrate side chains, particularly terminal sialic acids, in the constant region of the heavy chain, the conjugates may be prepared by binding the polycation to the carbohydrate side chain, using the method described by Wagner et al., 1991b.

Another aspect of the invention relates to binary and ternary complexes which are taken up into higher eucaryotic cells, containing nucleic acid and a conjugate of an internalizing factor and a substance having an affinity for nucleic acid. The binary complexes are characterized in that the internalizing factor is a virus which is bound to the substance having an affinity for nucleic acid via an antibody in such a way that it has the ability to penetrate into the cell as pan of the conjugate/nucleic acid complex and release the contents of the endosomes, in which the complex is located after entering the cell, into the cytoplasm. Ternary complexes further comprise an internalizing factor linked to a substance having affinity for a nucleic acid, wherein the internalizing factor is specific for a receptor on the surface of the higher eucaryotic cell. Such ternary complexes are useful for augmenting the uptake of nucleic acid into cells which have few or no adenoviral receptors.

As for the qualitative composition of the nucleic acid complexes, generally the nucleic acid to be transferred into the cell is determined first. The nucleic acid is defined primarily by the biological effect which is to be achieved in the cell and, in the case of use for gene therapy, by the gene or gene section which is to be expressed, e.g. for the purpose of replacing a defective gene, or by the target sequence of a gene which is to be inhibited. The nucleic acids to be transported into the cell may be DNAs or RNAs, whilst there are no restrictions imposed on the nucleotide sequence.

If the invention is applied on tumor cells in order to use them as a cancer vaccine, the DNA to be introduced into the cell preferably codes for a cytokine, e.g. IL-2, IL-4, IFN gamma, or TNF alpha. Combinations of cytokine-encoding DNAs may be particularly useful, e.g. IL-2 and IFN gamma. Another useful gene may be the multi-drug resistance gene (mdr).

It is also possible to introduce two or more different nucleic acid sequences into the cell, e.g. a plasmid containing cDNAs coding for two different genes under control of suitable regulatory sequences or two different plasmid constructs containing different cDNAs.

Therapeutically effective inhibiting nucleic acids for transfer into cells in order to inhibit specific gene sequences include gene constructs from which antisense-RNA or ribozymes are transcribed. Furthermore, it is also possible to introduce oligonucleotides, e.g. antisense oligonucleotides, into the cell. Antisense oligonucleotides comprise preferably 15 nucleotides or more. Optionally, the oligonucleotides may be multimerized. When ribozymes are to be introduced into the cell, they are preferably introduced as part of a gene construct which comprises stabilizing gene elements, e.g. tRNA gene elements. Gene constructs of this type are disclosed in European Patent Application Publication No. 0 387 775, the contents of which are fully incorporated by reference herein.

Apart from nucleic acid molecules which inhibit genes, e.g. viral genes, due to their complementarity, genes with different mode of inhibitory action may be employed. Examples are genes coding for viral proteins which have so-called trans-dominant mutations (Herskowitz, 1987). Expression of the genes in the cell yields proteins which dominate the corresponding wild-type protein and thus protect the cells, which acquire "cellular immunity" by inhibiting viral replication.

Suitable are trans-dominant mutations of vital proteins which are required for replication and expression, e.g. Gag-, Tat and Rev mutants which were shown to inhibit HIV replication (see Trono et al., 1989; Green et al., 1989; and Malim et al., 1989; the contents of each of which are fully incorporated by reference herein).

Another mechanism of achieving intracellular immunity involves expression of RNA molecules containing the binding site for an essential viral protein, e.g. so-called TAR decoys (see Sullenger et al., 1990, the contents of which are fully incorporated by reference herein).

Examples of genes which can be used in gene therapy and which can be enclosed in the cell as components of gene constructs by means of the present invention include factor VIII (hemophilia A) (see, e.g. Wood et al., 1984), factor IX (hemophilia B) (see, e.g. Kurachi, K. et al., 1982), adenosine deaminase (SCID) (see, e.g. Valerio, D. et al., 1984), α-1 antitrypsin (emphysema of the lungs) (see, e.g. Ciliberto, G. et al., 1985) or the cystic fibrosis transmembrane conductance regulator gene (see, e.g. Riordan, J. R. et al., 1989). These examples do not constitute a restriction of any kind.

As for the size of the nucleic acids, a wide range is possible; nucleic acid molecules of the order of about 0.15 kb (in case of a t-RNA gene containing a ribozyme) to about 50 kb or more may be transferred into the cells by means of the present invention; even smaller nucleic acid molecules may be applied as oligonucleotides.

When determining the molar ratio of antibody-polycation:nucleic acid it should be borne in mind that complexing of the nucleic acid(s) takes place. In the course of earlier inventions it had been established that the optimum transfer of nucleic acid into the cell can be achieved if the ratio of conjugate to nucleic acid is selected so that the internalizing factor-polycation/nucleic acid complexes are substantially electroneutral. It was found that the quantity of nucleic acid taken up into the cell is not reduced if some of the transferrin-polycation conjugate is replaced by non-covalently bound polycation; in certain cases there may even be a substantial increase in DNA uptake (Wagner et al., 1991a). It had been observed that the DNA inside the complexes is present in a form condensed into toroidal structures with a diameter of 80 to 100 nm. The quantity of polycation is thus selected, with respect to the two parameters of electroneutrality and the achievement of a compact structure, whilst the quantity of polycation which results from the charging of the nucleic acid, with respect to achieving electroneutrality, generally also guarantees compacting of the DNA.

A suitable method of determining the ratio of components contained in the complexes according to the invention is first to define the gene construct which is to be transferred into the cells and, as described above, to determine a virus which is suitable for the particular transfection. Then an antibody which binds to the virus is conjugated with a polycation and complexed with the gene construct. Starting from a defined quantity of virus, titrations are carried out by treating the target cells with this (constant) quantity of virus and decreasing concentrations of DNA complex. In this way the optimum ratio of DNA complex to virus is determined. In a second step the cells are treated with decreasing concentrations of the virus/DNA complex mixture (at a constant ratio of virus to complex) and the optimum concentration is determined.

Preferably, the virus is an adenovirus and the molar ratio of adenovirus to substance having an affinity to the nucleic acid is about 1/1 to about 1/100.

The length of the polycation is not critical, so long as the complexes are substantially electroneutral. The preferred range of polylysine chain lengths is from about 20 to about 1000 lysine monomers. However, for a given length of DNA, there is no critical length of the polycation. Where the DNA consists of 6,000 bp and 12,000 negative charges, the amount of polycation per mole DNA may be, e.g.:

60 molecules of polylysine 200

30 molecules of polylysine 400; or 120 molecules of polylysine 100, etc.

One of ordinary skill in the art can select other combinations of polycation length and amount of polycation with no more than routine experimentation.

The complexes according to the invention can be prepared by mixing the components nucleic acid and antibody-bound polycation, which are present in the form of dilute solutions. The DNA complexes can be prepared at physiological saline concentrations. Another possibility is to use high salt concentrations (about 2M NaCl) and subsequently adjust to physiological conditions by slow dilution or dialysis.

The best sequence for mixing the components nucleic acid, antibody-polycation conjugate and virus is determined by individual preliminary tests.

The invention relates in another aspect to a process for introducing nucleic acid into higher eucaryotic cells, in which the cells are brought into contact with the complexes according to the invention in such a way that the complexes are internalized and released from the endosomes.

The present invention relates in another aspect to pharmaceutical preparations containing as active component a complex consisting of therapeutically active nucleic acid, preferably as part of a gene construct, and an antibody coupled via a polycation. Preferably, this preparation is in the form of a lyophilisate or in a suitable buffer in the deep-frozen state and the virus preparation is mixed with the complex solution shortly before use. Possibly, the virus may already be contained in the pharmaceutical preparation, in which case it is in deep-frozen state. The components of the complex may be present as (partially) separate constituents of a transfection kit, which is also the subject of the present invention. In such a transfection kit, different DNAs and/or different internalizing factor conjugates may be provided separately from the virus preparation and/or the antibody conjugate. Depending on the constituents to be administered in a specific application, one of ordinary skill in the art can design different transfection kits to provide the widest possible flexibility. The transfection kit of the present invention comprises a carrier means having in close confinement therein one or more container means such as tubes, vials and the like, each of which contain the materials necessary to carry out the transfection of a higher eucaryotic cell in accordance with the present invention. In such a transfection kit, a first container means may contain one or more different DNAs. A second container means may contain one or more different immunologically-linked vital conjugates. A third container means may contain a second conjugate of an internalizing factor bound to a substance having an affinity for nucleic acid, e.g. polylysine, wherein the internalizing factor is specific for a surface receptor of a higher eucaryotic cell. Whether the constituents are supplied as a ready-to-use preparation or separately to be mixed immediately before use, depends, apart from the specific application, on the stability of the complexes, which can be determined routinely in stability tests. In a preferred embodiment, an antibody-linked chimeric adenovirus-polylysine conjugate is provided in one of the container means of a kit. In another preferred embodiment, one of the container means may also contain the internalizing factor bound to a substance having an affinity for a nucleic acid. Another container means may contain DNA.

For therapeutic purposes the preparations may be administered systemically, preferably by the intravenous route, to an animal, e.g. a human. The target organs for this type of administration may be, for example, the liver, spleen, lungs, bone marrow and tumors.

Recently, the feasibility of using myoblasts (immature muscle cells) to carry genes into the muscle fibers of mice was shown. Since the myoblasts were shown to secrete the gene product into the blood, this method may have a much wider application than the treatment of genetic defects of muscle cells like the defect involved in muscular dystrophy. Thus, engineered myoblasts may be used to deliver gene products which either act in the blood or are transported by the blood.

Examples for local application are the lung tissue (use of the composition according to the invention as part of a pharmaceutical composition comprising, e.g. a fluid for instillation or as an aerosol for inhalation). In addition, the pharmaceutical compositions of the invention may be administered by direct injection into the liver, optionally via the bile draining system, the muscle tissue or into a tumor or local administration in the gastrointestinal tract.

Therapeutic application may also be ex vivo, in which the treated cells, e.g. bone marrow cells, hepatocytes or tumor cells, are returned to the body (e.g. Ponder et al., 1991).

Any inert pharmaceutically acceptable carrier may be used, such as saline, or phosphate-buffered saline, or any such carrier in which the compositions of the present invention have suitable solubility properties for use in the method of the present invention. Reference is made to Remington's *Pharmaceutical Sciences*, Mack Publishing Co., Easton, Pa., Osol (ed.) (1980) for methods of formulating pharmaceutical compositions.

In order to determine the capacity for gene transfer of adenovirus-antibody-polycation/DNA complexes, a plasmid containing the gene coding for Photinus Pyralis Luciferase (De Wet et al., 1987) as reporter gene was used as the DNA. HeLa cells were used as target cells for the complexes; these cells have a defined population of cell surface receptors for adenoviruses (Philipson et al., 1968). When the components of the conjugate according to the invention (virus, antibody-polylysine-conjugate, DNA) were used in conjunction, high values were obtained for the expression of the luciferase reporter gene (FIG. 3): comparative experiments showed that the adenovirus only slightly increased the transfer of non-complexed plasmid-DNA. It was also found that DNA which was complexed with the antibody-coupled polylysine (without binding to the virus) was not appreciably taken up in HeLa cells. In sharp contrast to this, high gene expression values were obtained with the complex if the DNA was able to interact with the adenovirus by binding via the antibody. This effect was stopped when the virions were heat treated before the complexing. Since this treatment selectively removes the viral uptake functions without destroying the structural integrity of the virus (Defer et al., 1990), it can be concluded from these experiments that it is the specific uptake functions of the adenovirus which constitute the crucial contribution to the success of gene transfer. It was also found that competition for the heterologous epitope on the surface of the chimeric adenovirus by a specific, non-polylysine-bound monoclonal antibody also brings about a reduction in the net gene expression. This effect did not occur when an unspecific antibody was used. It is therefore the specific interaction between the antibody-bound DNA and the corresponding adenovirus surface epitope which is essential to the achievement of functional gene transfer by means of the complex. It was also found that polylysine-complexed DNA was not appreciably transferred into the target cells by the adenovirus. This is an indication that the gene transfer capacity of the complexes is not based on the condensing of DNA but depends on the antibody-mediated binding of the reporter gene to the virion.

In accordance with this, the use of a virus which did not have the epitope recognized by the polylysine-coupled antibody could not achieve the high gene expression values achieved by a virus which did have this epitope. However, this virus was able to increase the extent of gene transfer above the background level. Since it is known that adenoviruses are capable of nonspecifically augmenting the cellular uptake of macromolecules through the liquid phase (Defer et al., 1990), this result was not unexpected. The fact that this non-specific transport brought about a significantly lower expression of the reporter gene than the specific virus which was able to bind to the antibody-polylysine/DNA complex demonstrates the importance of specific binding of the components of the complex.

Figure 4:
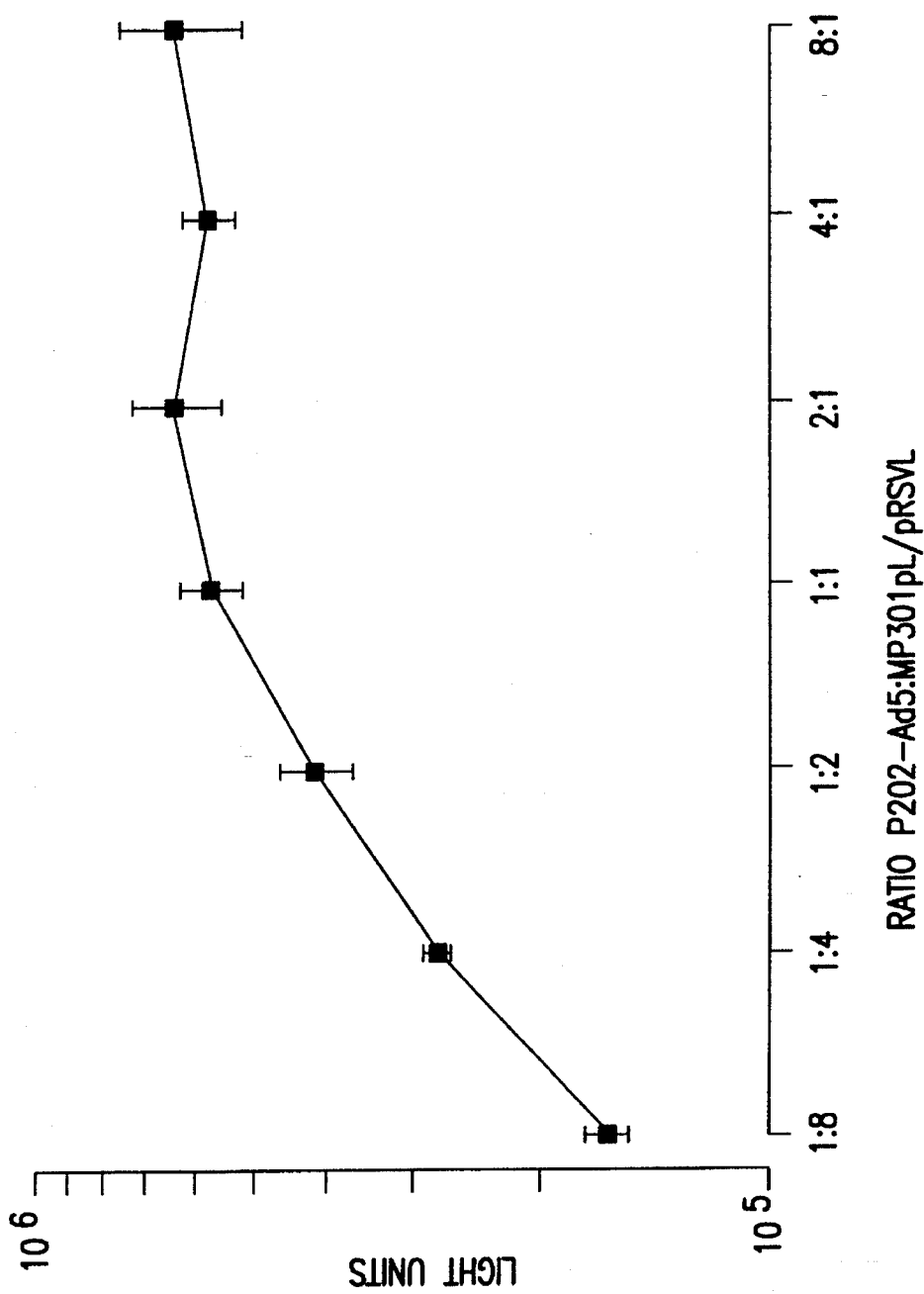
FIG. 4: Determining the optimum ratio of adenovirus and polylysine-antibody-complexed DNA to mediate gene transfer. A fixed amount of antibody-polylysine-DNA complex was combined with various molar ratios of epitope-tagged adenovirus and evaluated for the capacity to mediate gene transfer to HeLa cells.

The interaction of plasmid DNA with polylysine conjugates results in significant structural changes in the DNA molecule, which are most clearly characterized by striking condensation into a toroidal structure of 80 to 100 nm (Wagner et al., 1991a). The diameter of the virus is of the order of 70 to 80 nm (Philipson, 1983). It was therefore assumed, on the basis of steric considerations, that the optimum ratio of adenovirus to antibody-polylysine-complexed DNA should be no more than 1:1. Furthermore, the diameter of the coated pits by means of which the initial uptake step of receptor-mediated endocytosis is carried out, is about 100 nm (Darnell et al., 1975). On the basis of this fact it was assumed that multimers exceeding this size would be restricted in their uptake capacity. Within the scope of the present invention these correlations were analyzed, whilst the use of adenovirus in molar excess relative to the antibody-polylysine-complexed DNA showed that the maximum expression of reporter gene was achieved at a ratio of 1:1 (FIG. 4). The optimum conjugate, within the scope of the experiments carried out, was therefore found to be one which consists of a single adenovirus internalizing domain in conjunction with a single antibody-polylysine/DNA binding domain.

Next, the gene transfer efficiency of adenovirus-antibody-polycation conjugates having this optimum ratio was investigated. If logarithmic dilutions of the complex were added to the target cells, there was a corresponding logarithmic reduction in expression of the reporter gene (FIG. 5), whilst it was noticeable that $10^7$ DNA molecules, applied to $10^6$ HeLa cells using this vector system, resulted in the detectable expression of the reporter gene. Surprisingly, therefore, efficient expression of a foreign gene was achieved with as few as 10 DNA molecules per cell in the form of adenovirus-polycation-DNA complexes.

Therefore, with regard to the magnitude of DNA uptake, the conjugates according to the invention show clear superiority over the DNA gene transfer vectors, which are required in numbers of approximately 500,000 DNA molecules per cell (Felgner et al., 1987, Felgner et al., 1989, Maurer, 1989). Since these methods efficiently convey the majority of the DNA into the target area of the cells, namely the cytosol (Felgner et al., 1989, Malone et al., 1989, Loyter et al., 1982), the efficiency of the conjugates according to the invention may possibly not be based exclusively on the increase in release of the foreign DNA into the cytoplasm; other mechanisms on the route of gene transfer may also be enhanced.

Having now generally described the invention, the same will be more readily understood through reference to the following examples which are provided by way of illustration, and are not intended to be limiting in any way. All patents and publications cited herein are incorporated by reference herein in their entirety.

EXAMPLES

The invention is illustrated by means of the following Examples:

Example 1

Figure 2A:
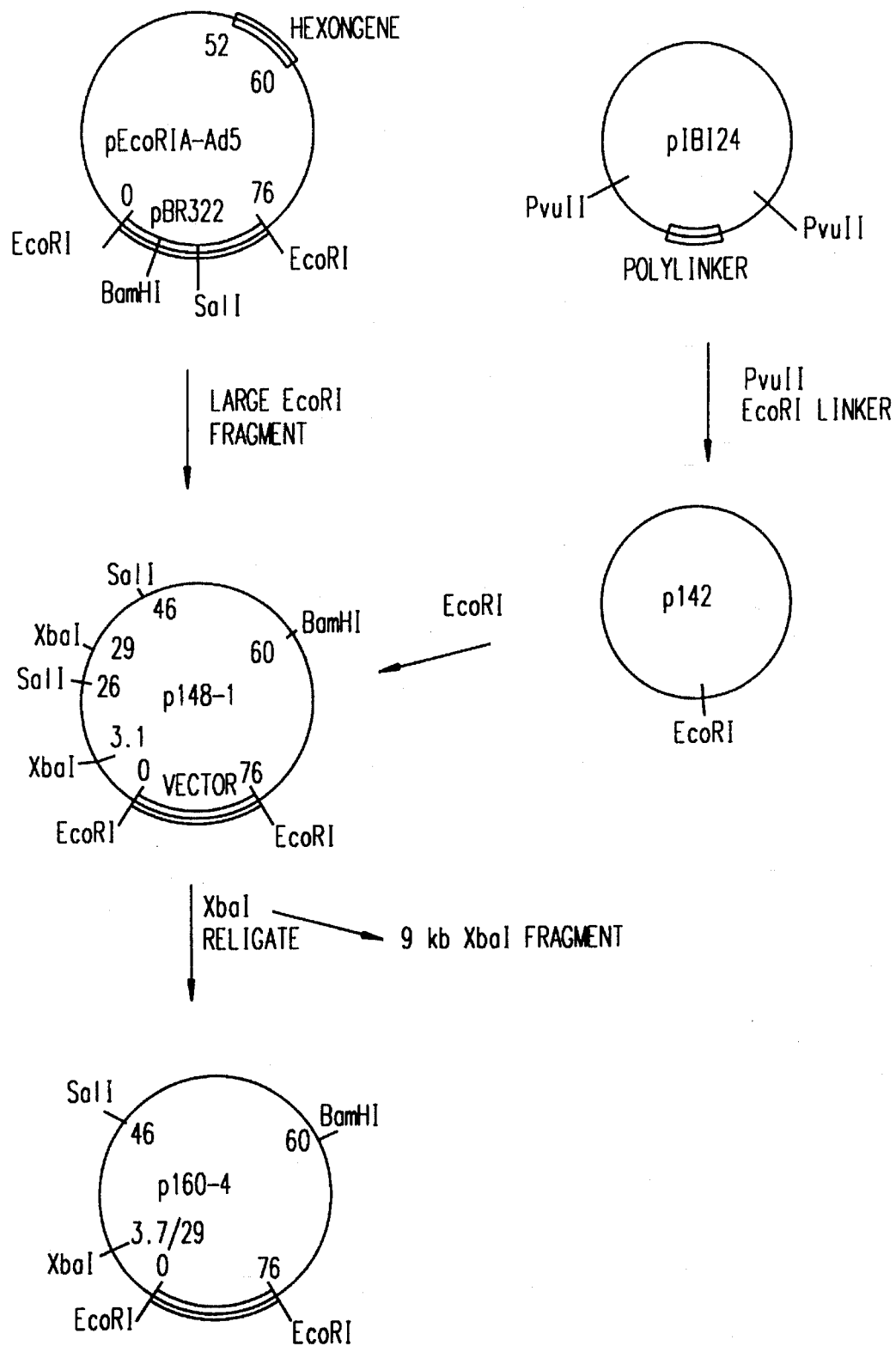
FIGS. 2A–2B: Preparation of the chimeric adenovirus Ad5-P202.
Figure 2B:
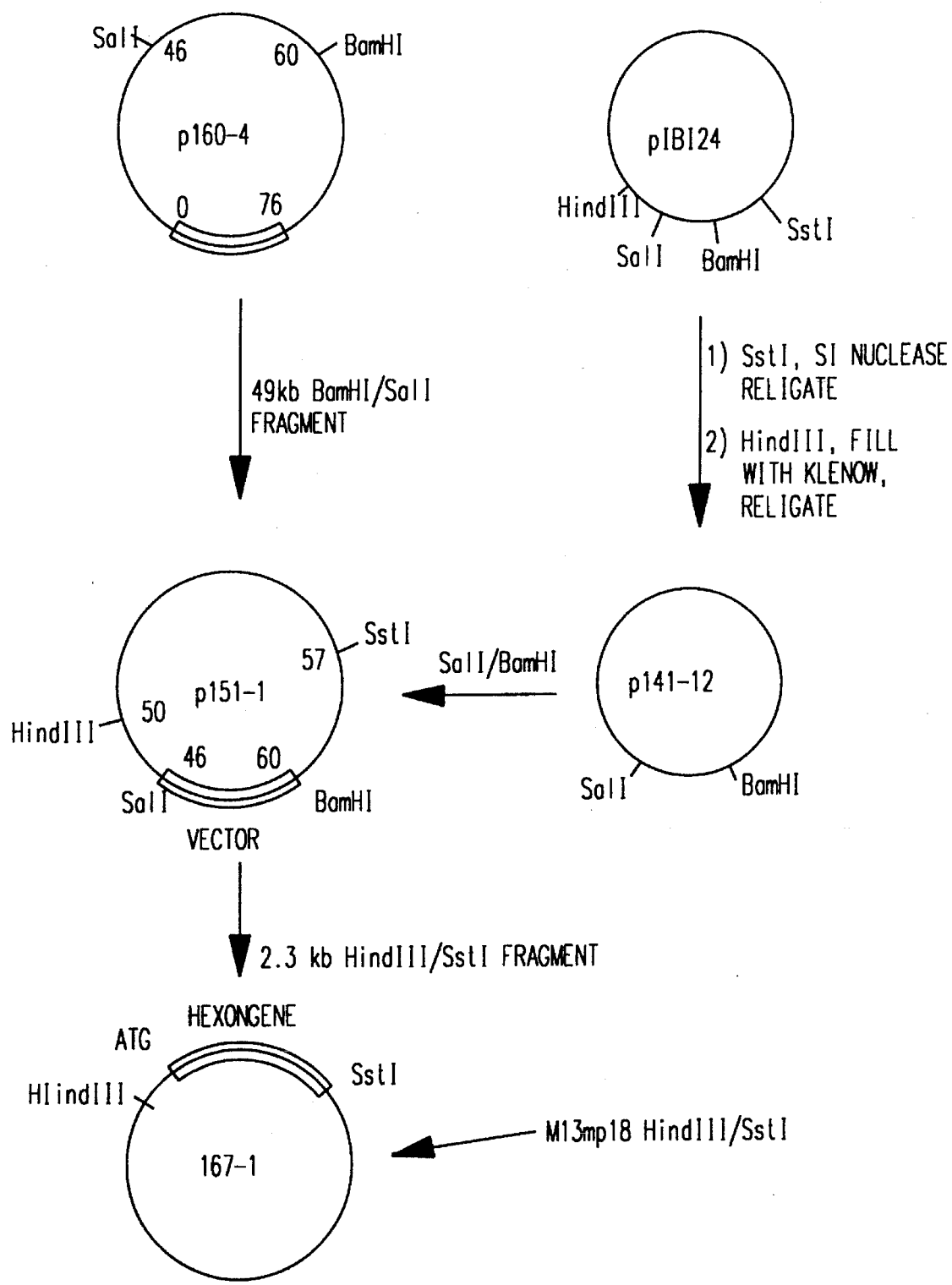

Preparation of antibody-polylysine conjugates
1) Preparation of the chimeric adenovirus Ad-P202
In order to make changes in the Ad5 hexon gene it was first necessary to subclone the gene. The plasmid pEcoRIA-Ad5 (Berkner and Sharp, 1983) contains the left-hand part of the adenovirus genome of map unit (m.u.) 0 to 76. The hexon gene is between m.u.52 and m.u.60. A 2.3 kbp HindIII/SstI-fragment contains that part of the hexon gene in which the change is to be made. Since a plurality of HindIII and SstI sites are contained in pEcoRIA-Ad5 it was necessary to construct several intermediate plasmids in order to be able to assemble the altered hexon gene in the original plasmid. A SalI/BamHI fragment (m.u. 46 to 60) contains the hexon gene without any additional HindIII or SstI sites. First of all, the adenovirus DNA was recloned from m.u. 0 to 76 by using a vector designated p142 (derived from the commercially obtainable plasmid pIBI24 (IBI, Inc.) by restriction digestion with PvuII, followed by the insertion of an EcoRI linker) which contains no SstI or BamHI sites. Then the SalI sites at m.u. 26 were eliminated by deleting the XbaI fragment (m.u. 3.7 to 29); the resulting vector was designated p141-12. Finally, the desired HindIII/SstI-fragment was cloned in M13mp18 and was therefore ready for mutagenesis. Site directed mutagenesis was carried out with one of the resulting clones using the method described by Kunkel, 1985. The codons 188 to 194 of the hexon gene were removed and at this position a unique PmlI-site occurring only once was introduced. The resulting clone (167-1) was then cut with PmlI and a double stranded oligonucleotide coding for the amino acids 914–928 of the *Mycoplasma pneumoniae* P1-protein was inserted (Inamine et al., 1988). This insertion is in loop 11 of the hexon protein, which is located on the outer surface of the viron (Roberts et al., 1986). The P1-sequence contains an epitope which is recognized by the monoclonal antibody 301, the preparation of which is described hereinafter. The modified HindIII/SstI-fragment was isolated from p167-1 and ligated back into the original plasmid pEcoRIA-Ad5. The preparation of Ad-P202 is shown in FIG. 2.
2) Preparation of a monoclonal antibody with specificity for the chimeric adenovirus (MP301)
a) Immunization
The monoclonal antibody was prepared by standard methods.
The *Mycoplasma pneumoniae* strain M-129 (ATCC#29342) was used as the antigen. After cultivation in a culture flask (Hu et al., 1977) it was washed 3 times with PBS, *Mycoplasma pneumoniae* was harvested and taken up in 0.5 ml of PBS. 10 µg of the antigen were used for immunization:

3 female BALB/c mice about six weeks old were immunized in accordance with the following protocol:
1st immunization: about 10 μg of antigen per mouse in complete Freund's adjuvant by intraperitoneal route.
2nd immunization: about 10 μg of antigen per mouse in incomplete Freund's adjuvant by subcutaneous route, 3 weeks after the first immunization.
3rd immunization: about 10 μg of antigen per mouse in incomplete Freund's adjuvant by intraperitoneal route, 2 weeks after the second immunization.

One week later, samples of serum taken from the mice and the serum titres were measured. The mouse with the highest titre was boosted by i.v. injection of 10 μg antigen into the tail; the spleen cells of this mouse were taken out after 3 days for fusion with hybridoma cells.

b) Fusion:

About $10^8$ spleen cells were fused with about $10^8$ myeloma cells of the line SP2/0 Ag14 (ATCC CRL-1581) in the presence of PEG 4000 (50% in serum-free culture medium) using the method of Köhler and Milstein, 1975. Then the cells were grown for 2 weeks in HAT-selection medium, then for one week in HT-medium and finally in normal culture medium (DMEM plus 10% FCS plus penicillin, streptomycin). By means of radioimmuno-sorbent assay (RIA) screening was carried out for antibody-producing clones and specificity for the *Mycoplasma pneumoniae* P1 protein was determined using Western blot. The "soft agar" method was used to obtain monoclones.

c) Investigation of the monoclonal antibody MP301 for neutralizing effect of adenovirus Ad-P202

In order to determine whether the monoclonal antibody MP301 neutralizes the ability of the virus to infect cells, the titre of Ad-P202 was determined once with and once without the addition of antibody (7 μg/ml), using HeLa-cells (approximately 50% confluent in 2% FCS/DMEM on 96-well plates) as the target cells. Serial dilutions were prepared of Ad-P202 which were applied to the HeLa-titre plates with or without antibody. The plates were incubated for 48 hours at 37° C., 5% $CO_2$, stained with crystal violet and investigated for IC 50 (inhibition concentration, about 50% cell lysis). The titre of 1:2048 was obtained with and without antibody.

d) Preparation of MP301-polylysine conjugates

Coupling of the monoclonal antibody to polylysine was carried out using the method described by Wagner et al., 1990, and in EP-A1 388 758. 20.6 nmol (3.3 mg) of the monoclonal antibody MP301 in 1 ml of 200 mM HEPES pH 7.9 were treated with a 5 mM ethanolic solution of SPDP (100 nmol). After 3 hours at ambient temperature the modified antibody was gel-filtered over a Sephadex G-25 column, thereby obtaining 19 nmol of antibody modified with 62 nmol of dithiopyridine linker. The modified antibody was allowed to react with 3-mercaptopropionate-modified polylysine (22 nmol, average chain length 300 lysine monomers, FITC-labelled, modified with 56 nmol mercapto-propionate linker) in 100 mM HEPES pH 7.9 under an argon atmosphere. Conjugates were isolated by cation exchange chromatography on a Mono S HR5 column (Pharmacia). (Gradient: 20 to 100% buffer B. Buffer A: 50 mM HEPES pH 7.9; buffer B: buffer A plus 3M sodium chloride. The product fraction eluted at a salt concentration of between 1.65M and 2M. Dialysis against HBS (20 mm HEPES pH 7.3, 150 mM NaCl) produced a conjugate consisting of 9.1 nmol MP301 and 9.8 nmol polylysine.

Example 2

Gene transfer by means of adenovirus-polycation-DNA-complexes in Eucaryotic cells In the course of the experiments carried out in this Example, various combinations of specific and non-specific complex components were examined for their ability to transport a reporter gene into HeLa and other cells.

Complexing of DNA with the antibody-coupled polylysine was carried out by diluting 6 μg of purified pRSVL-DNA in HBS (150 mM NaCl, 20 mM HEPES, pH 7.3) to a total volume of 350 μl and purifying it with 9.5 μg of MP301pL in 150 μl of total volume of the same buffer. (pRSVL contains the Photinus pyralis luciferase gene under the control of the Rous Sarcoma virus LTR enhancer/promoter (Uchida et al., 1977, De Wet et al., 1987), prepared by Triton X Lysis Standard Method (Maniatis), followed by CsCl/EtBr equilibrium density gradient centrifugation, decolorizing with butanol-1 and dialysis against 10 mM tris/HCl pH 7.5, 1 mM EDTA in 350 μl HBS (150 mM NaCl, 20 mM HEPES, pH 7.3).) The quantity of antibody-coupled polylysine is based on a calculation of the quantity required to achieve electroneutrality of the imported DNA. The polylysine-antibody-complexed DNA was diluted in HBS to a final concentration of $2 \times 10^{11}$ DNA molecules per ml.

The adenovirus P202-Ad5 was diluted in ice-cold DMEM, supplemented with 2% FCS, to a final concentration of $2 \times 10^{11}$ virus particles per ml. Equal volumes of antibody-polylysine DNA and virus were combined and incubated for 30 minutes at ambient temperature. The target cells used for the gene transfer were HeLa cells which had been grown in DMEM medium supplemented with 5% FCS, 100 I.U. penicillin/ml and 100 μg streptomycin/ml, in 60 mm tissue culture dishes (300,000 cells). For comparison to HeLa cells, the cell lines HBE1, KB and MRC-5 were evaluated. HBE1, a respiratory cell line, was grown in F12-7X medium as described by Willumson et al., 1989. KB and MRC-5 were grown in Eagle's minimal essential medium/10% heat-inactivated FCS/penicillin at 100 international units per ml/streptomycin at 100 μg per ml/10 mM nonessential amino acids/2 mM glutamine.

Figure 3:
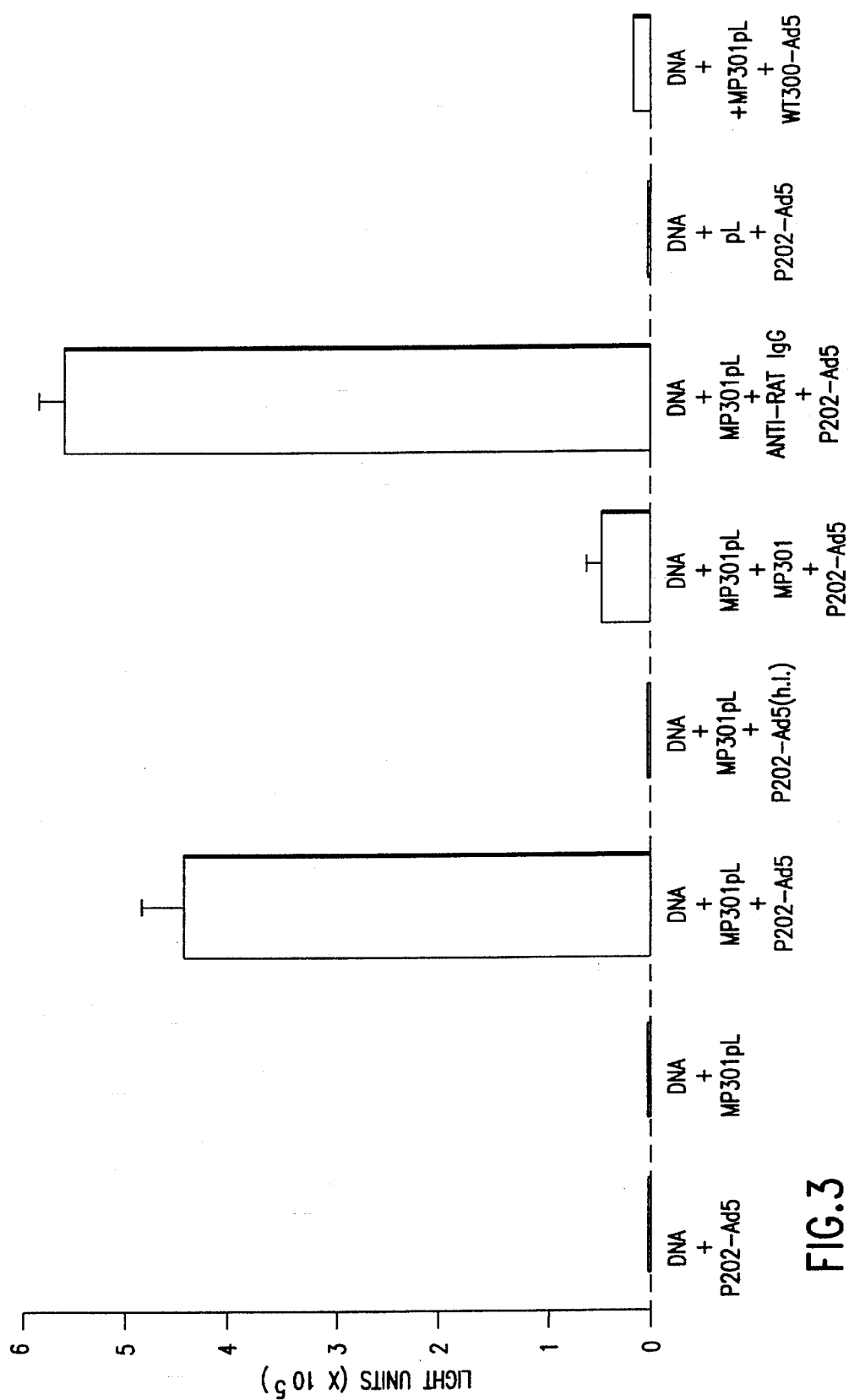
FIG. 3: Gene transfer using adenovirus-polycation-DNA complexes. Various combinations of specific and nonspecific complex components were evaluated for the capacity to mediate reporter gene transfer to HeLa cells. Reporter plasmid pRSVL (6 µg) [DNA] was complexed with either antibody-polylysine (9.5 µg) [MP301pLys] or equimolar amounts of unconjugated polylysine (4 µg) [pLys]. The complexed DNA was diluted prior to combination with adenovirus. Epitope-tagged virus [P202-Ad5] or irrelevant adenovirus [WT300] ($2.5 \times 10^{10}$ particles) was added to the DNA complexes ($2.5 \times 10^{10}$ DNA molecules) in the absence or presence of non-lysinated monoclonal antibody [MP301] or equimolar amounts of irrelevant monoclonal antibody [anti-rat IgG]. For some experiments adenovirus P202 was heat inactivated [P202-Ad5(h.i.)] prior to combination with antibody-polylysine-DNA complexes. After incubation, cell lysates were evaluated for luciferase reporter gene expression.

Before application of the transfection medium, the plates were cooled at 4° C. for 30 minutes, the medium was removed, 1 ml of transfection medium was added and the cells were incubated for 2 hours at 4° C. This step was carried out in order to bring about binding of the DNA complexes to the cells without them being internalized. After this binding step, the plates were washed three times with ice-cold 2% FCS/DMEM in order to eliminate any non-bound reaction components in the liquid phase. After the addition of 2 ml of ice-cold 2% FCS/DMEM the plates were slowly heated. Then the plates were placed in an incubator for 16 hours (37° C., 5% $CO_2$). In order to measure the expression of reporter gene, cell lysates were prepared, standardized in terms of their total protein content and investigated for luciferase activity exactly as described by Zenke et al., 1990. (The luminometer was calibrated so that one picogram of luciferase yields 50,000 light units.)

pRSVL reporter plasmid DNA was combined with adenovirus P202-Ad5 without having been previously complexed with the polylysine antibody conjugate (DNA+P202-Ad5). Furthermore, pRSVL-DNA, complexed with the antibody-coupled polylysine, was investigated in the absence of the specific virus (DNA+MP301pL) and these two reaction media were compared with a reaction medium containing the total combination of the complex components (DNA+MP301pL+P202Ad5). Analogously, the complexes were investigated for their ability to perform gene transfer by using a specific antibody which had been heat inactivated before complexing (45° C., 30 min)(DNA+MP301pL+P202-Ad5). Competition experiments were carried out with the specific adenovirus in the presence of the polylysine-coupled antibody MP301 plus a ten-fold molar excess of non-polylysine-coupled MP301 (DNA+MP301pL+MP301+P202-Ad5) or in the presence of MP301pL and a ten-fold molar excess of non-coupled irrelevant monoclonal antibody, anti-rat-IgG (DNA+MP301pL+anti-rat IgG+P202-AD5). Furthermore, before incubation with the specific virus, the reporter plasmid DNA was complexed with non-conjugated polylysine (4 μg) in an amount equimolar to the antibody-coupled polylysine (DNA+pL+P202-Ad5). The complex forming reactions using the adenovirus WT300, which lacks the epitope recognized by MP301, were carried out exactly as for the specific virus P202-AD5. The experiments were carried out three times in all. The results are shown in FIG. 3; the data represent mean values± SEM. The dotted horizontal line shows the background signal of untreated HeLa cells.

Results

To evaluate the capacity of the adenovirus-polylysine-DNA complexes to mediate gene transfer, a plasmid encoding the firefly luciferase gene was used as a reporter (De Wet et al., 1987). The epithelial cell line HeLa was used as a target for the complexes as these cells possess a defined population of cell surface receptors for adenoviruses (Philipson et al., 1968). When employed in combination, the components of this conjugate system mediated high levels of expression of the luciferase reporter gene (FIG. 3). Control experiments demonstrated that the adenovirus did not significantly augment target cell delivery of uncomplexed plasmid DNA. Reporter DNA complexed by the polylysine monoclonal antibody was also not appreciably transferred to the target HeLa cells. In marked contrast, when the monoclonal antibody-bound DNA was allowed to interact with the epitope-tagged adenovirus, the resulting complex mediated high level gene expression. This effect was abolished by heat treatment of the virions prior to complex formation. Since heat treatment selectively abrogates adenoviral entry functions without perturbing viral structural integrity (Defer et al., 1990), it is apparent that the specific internalization functions of the adenovirus comprise a significant component of the gene transfer capacity of the complexes. Competition for the heterologous epitope on the surface of the chimeric adenovirus by non-lysinated specific monoclonal antibody also attenuated the net gene expression accomplished by the complex. This effect was not seen with an irrelevant monoclonal antibody. Thus, the specific interaction between the monoclonal antibody-bound DNA and the corresponding adenoviral surface epitope is important in permitting functional gene delivery by the complex. Consistent with this concept, an adenovirus lacking the epitope recognized by the polylysine antibody was not capable of mediating the high levels of gene expression achieved by the virus which possessed this epitope. Further, polylysine-complexed DNA was not appreciably transferred to target cells by the adenovirus, indicating that the gene transfer capacity of the complexes was not on the basis of DNA condensation but contingent upon the antibody-mediated attachment of the reporter gene to the virion.

Example 3

Determination of optimum ratio of adenovirus and antibody-polylysine/DNA for gene transfer In the experiments carried out, the results of which are given in FIG. 4, adenovirus-antibody-polylysine/DNA complexes with the complex components in various proportions were examined for their ability to permit gene transfer into HeLa cells. The complex forming reactions were carried out as given in Example 2, except that $2.5 \times 10^{10}$ DNA molecules complexed with the antibody-polylysine conjugate were used, with different amounts of the specific adenovirus P202-Ad5. The cultivation of the cells, the application of the complexes to the cells, incubation of the cells and measurement of the reporter gene expression were as in Example 2. The data shown represent mean± SEM from four different experiments.

Results

Interaction of plasmid DNA with polylysine conjugates results in significant structural alterations of the DNA molecule, characterized most prominently by marked condensation into a 80–100 nm diameter toroid structure (Wagner et al., 1991). The diameter of the adenovirus is also on the order of 70–80 nm (Philipson, 1983). When evaluated experimentally, it was shown that adenovirus input in molar excess of polylysine-antibody complexed DNA yielded a plateau of reporter gene expression at a ratio of unity (FIG. 4). Thus, the optimized conjugate consists of a single adenoviral cognate domain in association with a single polylysine-antibody DNA binding domain.

Example 4

The measurement of the gene transfer performance of adenovirus-polycation-DNA complexes Limiting dilutions of the complex, prepared exactly as in Example 2, were investigated to see how effective they are at enabling the detectable expression of the reporter gene in HeLa cells. After complex formation, logarithmic dilutions of the complex in 2% FCS/DMEM were prepared. 1 ml aliquots of the various dilutions were applied to 60 mm tissue culture dishes which contained $5 \times 10^5$ HeLa cells. After one hour incubation (37° C., 5% $CO_2$), 3 ml of 5% FCS/DMEM were added and the plates were incubated for a further 16 hours under the same conditions. The reporter gene expression was measured as in Example 2. The values for luciferase expression given in FIG. 5 correspond to the mean values± SEM from 3 or 4 experiments. The dotted horizontal line shows the background signal of untreated HeLa cells.

Results

Figure 5:
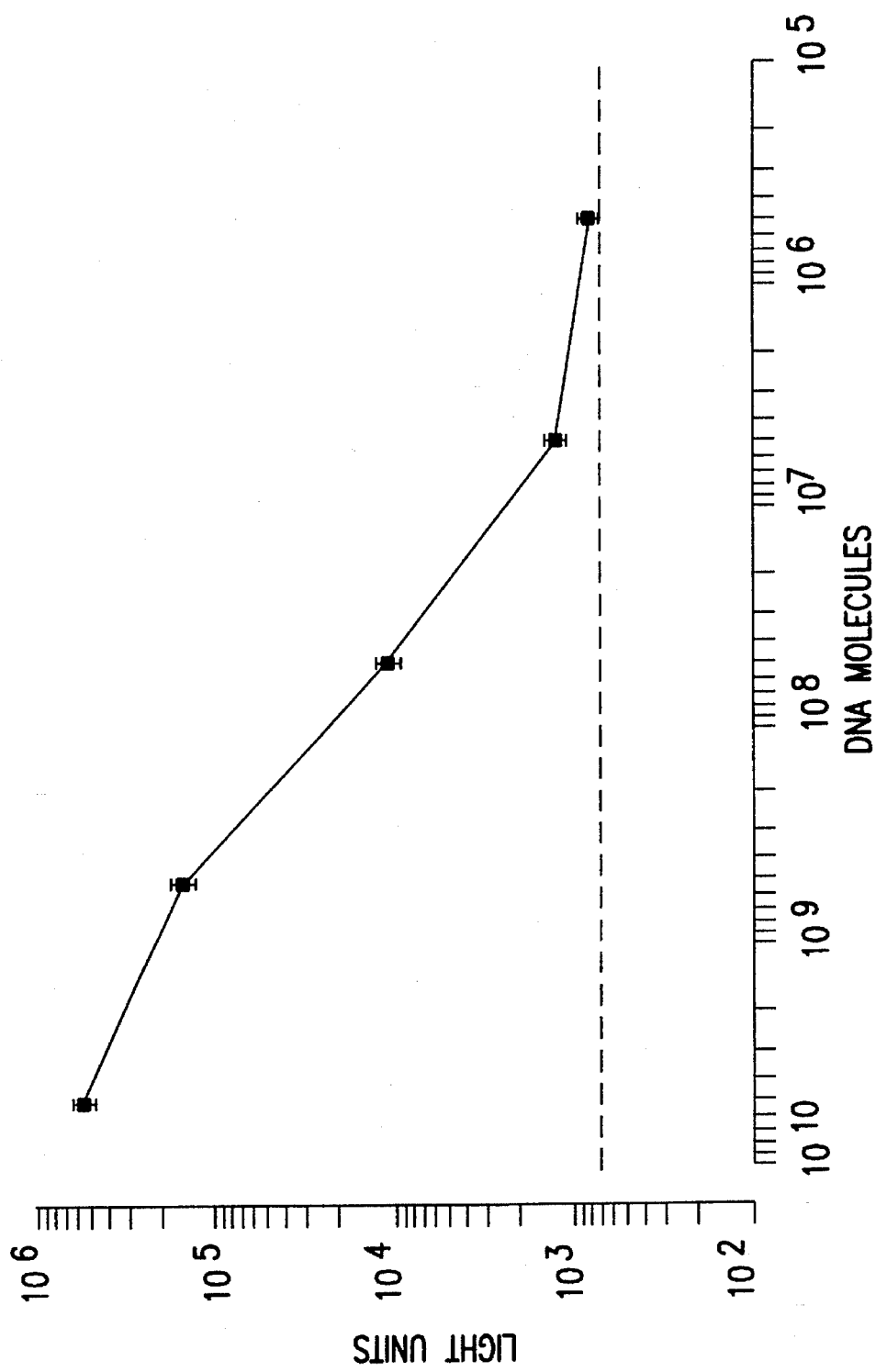
FIG. 5: Determining the gene transfer achieved by means of adenovirus-polycation-DNA complexes. Limiting dilutions of the complex were evaluated for the capacity to mediate detectable levels of luciferase gene expression in HeLa cells. Dotted line indicates background levels of luciferase gene expression in untreated HeLa cells.

The efficiency of gene transfer of the adenovirus-polylysine conjugates at the optimized ratio of 1:1 was examined. Logarithmic dilutions of the complex administered to target cells yielded a corresponding logarithmic decrease in reporter gene expression (FIG. 5). Significantly, $5 \times 10^6$ DNA molecules delivered by this vector system to $5 \times 10^5$ HeLa cells produced detectable levels of reporter gene expression. Thus, administration of as few as 10 DNA molecules per cell in the form of adenovirus-polylysine-DNA complexes accomplished detectable foreign gene expression. This is in marked contrast to the amount of input DNA required by DNA-mediated gene transfer vectors, where on the order of 500,000 DNA molecules per cell are required (Felgner et al., 1987; Felgner et al., 1989; Maurer, 1989).

Figure 6:
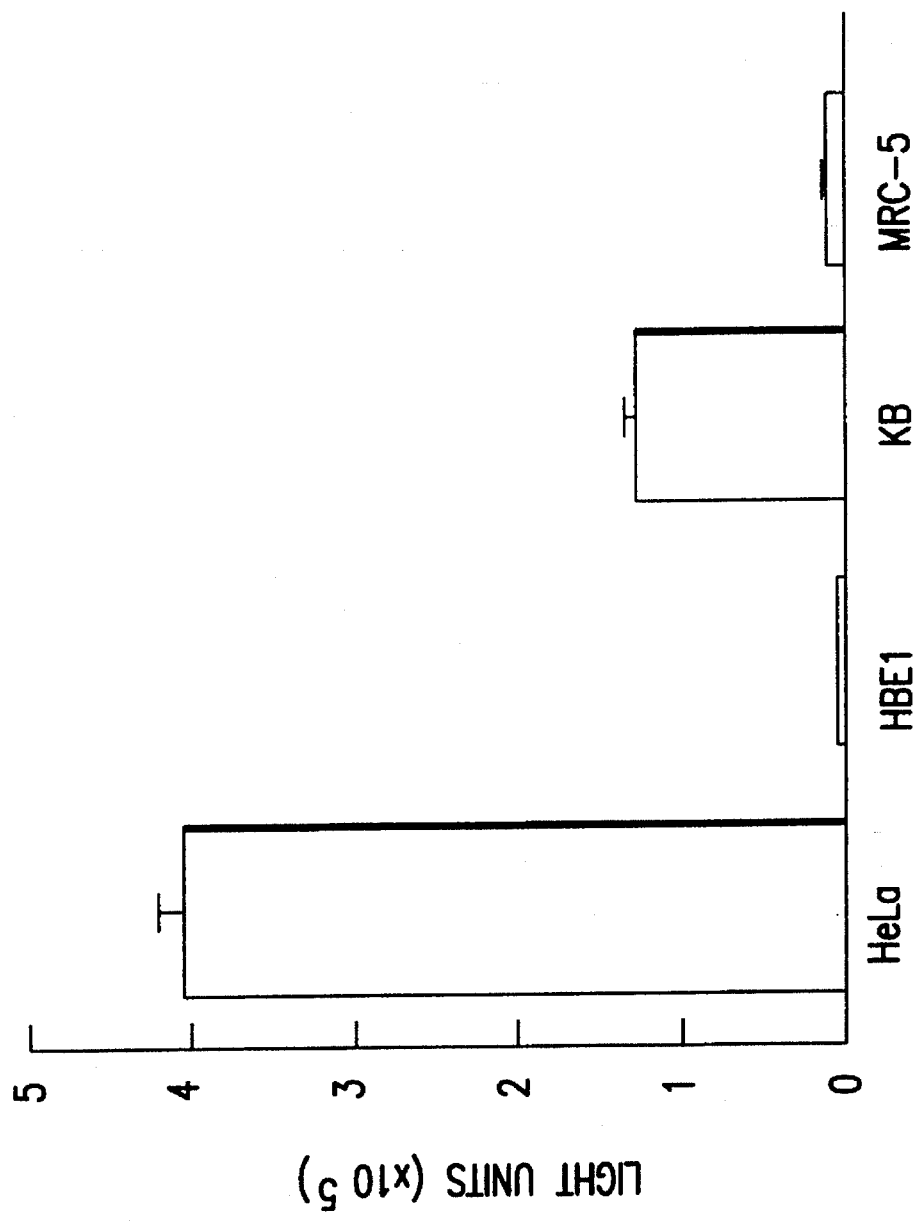
FIG. 6: Gene transfer to various cell lines mediated by adenovirus-polylysine-DNA complexes. Epitope-tagged adenovirus P202-Ad5 ($2.5\times10^{10}$ particles) was added to complexes formed between antibody-polylysine MP301pLys and reporter plasmid DNA pRSVL. The resulting adenovirus-polylysine-DNA complexes were incubated with the cell lines HeLa, HBE1, KB, and MRC-5 as for FIG. 3. Reporter gene expression in the cell lysates was evaluated as before.

In the configuration of the adenovirus-polylysine-DNA complexes, the adenovirus moiety functions both in the capacity of an endosome disruption agent and as the ligand domain of the complex. Thus, the gene transfer efficiency of the complexes for a given target cell should reflect the relative number of adenoviral cell surface receptors. Both HeLa and KB, cell lines known to possess high levels of adenoviral receptors (Philipson et al., 1968), demonstrated a corresponding high degree of susceptibility to gene transfer via adenoviral-polylysine-DNA complexes (FIG. 6). In contrast, the relatively low number of adenoviral receptors characterizing MRC-5 (Precious and Russell, 1985) and HBE1 (data not shown) is reflected in a lower level of gene transfer to these cells lines mediated by the complexes.

Example 5

The Preparation of Chimeric Complexes Containing Adenovirus and Human Transferrin To prepare ternary complexes containing a combination of adenovirus and human transferrin domains, the epitope-tagged adenovirus P202-Ad5 ($2.5 \times 10^{10}$ particles) was diluted in 750 µl 2% FCS/DMEM and combined with polylysine monoclonal antibody MP301pLys (2 µg) diluted in 250 µl HBS. Incubation was performed for 30 minutes at room temperature. Plasmid DNA pRSVL (6 µg) diluted in 250 µl HBS was then added to the mixture and incubated for an additional 30 minutes at room temperature. The resulting adenovirus-polylysine-DNA complexes were predicted to possess incompletely condensed DNA based upon total polylysine content. To complete DNA condensation and contribute a human transferrin moiety to the complexes, human transferrin polylysine conjugates (Wagner et al., 1990) (9 µg) diluted in 250 µl HBS were added to the adenovirus-polylysine-DNA complexes. A final incubation of 30 minutes at room temperature was performed. The resulting chimeric complexes were incubated with tissue culture cells to achieve specific binding of the formed complexes (4° C., 2 hours). The plates were then washed three times with ice-cold 2% FCS/DMEM and returned to the incubator (37° C., 5% $CO_2$) for 16 hours after the addition of 2 ml 2% FCS/DMEM. Evaluation of reporter gene expression was as before.

Results

Specific internalization of molecular conjugate gene transfer vectors is dictated by tropism of the conjugate ligand domain for receptors on the cell surface. Subsequent to internalization, gene transfer efficiency is limited by the conjugate's lack of specific mechanism to escape entrapment within the cell vesicle system. Adenovirus-polylysine-DNA complexes exploit adenoviral-mediated endosome disruption to enhance gene transfer efficiency. In this specific configuration, however, the adenoviral domain also functions as the ligand moiety of the conjugate, limiting the efficacy of this vector to target cells containing surface receptors for adenovirus. As an alternative means to exploit the endosome disruption capacity of the adenovirus, ternary complexes were constructed that contained an alternate cell surface ligand moiety in conjunction with an adenovirus moiety. In this arrangement, it was hypothesized that the adenovirus moiety would mediate endosome disruption after internalization via the adenoviral pathway or the pathway of the alternate ligand. To evaluate this concept, ternary complexes were constructed that contained a human transferrin ligand domain in conjunction with an adenoviral domain. The gene transfer efficiency of these chimeric complexes was compared to human transferrin-polylysine-DNA complexes (Wagner et al., 1990) and adenovirus-polylysine-DNA complexes in HeLa cells, a cell line containing cell surface receptors for both adenovirus and transferrin (Heubers and Finch, 1987). The ternary complexes accomplished significantly greater levels of reporter gene expression than the conjugates that possessed exclusively transferrin or adenovirus ligand domains (FIG. 7A). The magnitude of this augmentation was clearly not on the basis of an additive effect of human transferrin-polylysine-DNA complexes plus adenovirus-polylysine-DNA complexes. Since the ternary complexes may be internalized via the adenoviral or transferrin pathways, this apparent cooperativity suggests that the adenovirus domain facilitates entry via either pathway, likely on the basis of adenovirus-mediated endosomolysis.

Figure 7B:
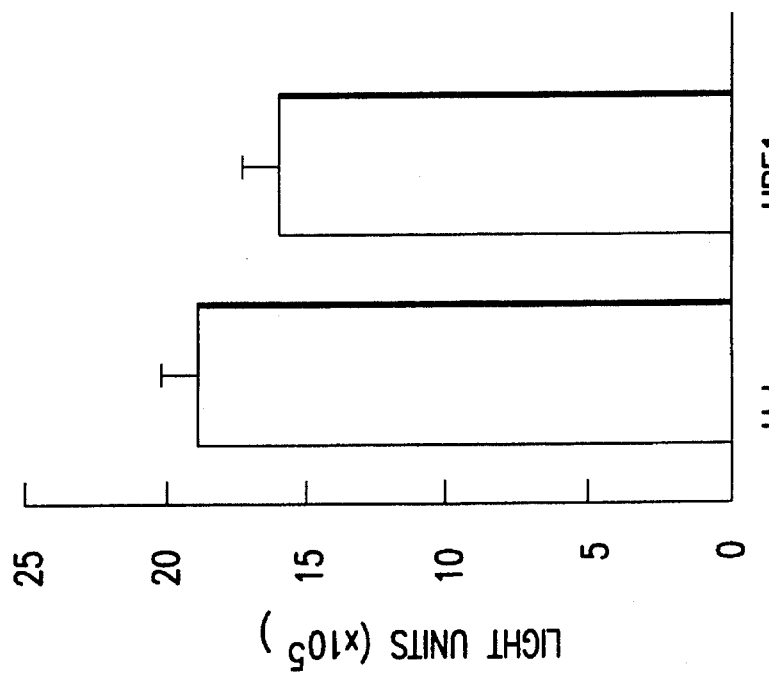
FIGS. 7A and 7B: Gene transfer mediated by chimeric complexes containing adenovirus and human transferrin.
Figure 7A:
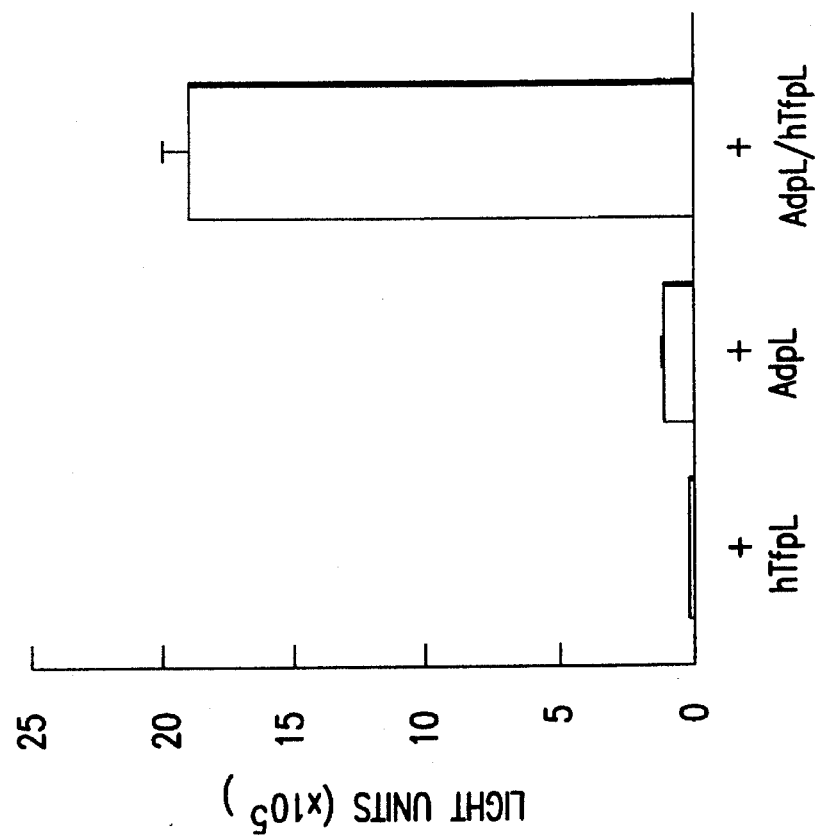

To demonstrate the selective employment of the endosome disruption capacity of the adenoviral domain of the ternary complex, the chimeric complexes were delivered to cell lines that exhibited variable susceptibility to adenovirus-polylysine-DNA complexes (FIG. 7B). The respiratory epithelial cell line HBE1 shows very low levels of gene transfer mediated by adenovirus-polylysine-DNA complexes, compared to HeLa cells (FIG. 6), reflecting the relatively low cell surface population of adenoviral receptors characterizing this line. In marked contrast, employment of the adenovirus-transferrin ternary complexes resulted in levels of gene expression comparable to those seen in HeLa cells. The susceptibility of this cell line to gene transfer via the ternary complexes is consistent with the concept that the adenoviral domain is internalized via the transferrin pathway, where it augments gene transfer by mediating endosome disruption. Thus, it appears feasible to selectively exploit the endosomolysis property of adenovirus in the design of molecular conjugate vectors that thereby possess the capacity to escape the cell vesicle system.

Example 6

Direct in vivo Gene Transfer to Airway Epithelium Employing Adenovirus-Polylysine-DNA Complexes In the present example, the direct in vivo gene transfer to the respiratory epithelium is accomplished in a rodent model using adenovirus-polylysine-DNA complexes. This establishes the feasibility of this approach as a method to accomplish transient gene expression in the respiratory epithelium. The capacity to achieve genetic modification of the airway epithelial cells in situ offers a potential strategy to accomplish gene therapy for disorders afflicting the airway epithelium.

METHODS

Preparation of gene transfer vectors. Human transferrin-polylysine-DNA complexes (hTfpL) were prepared by combination of (8.0 µg) human transferrin-polylysine (Serva Biochemical) in 150 µl NaCl 150 mM/HEPES 20 mM, pH 7.3 (HBS) plus 6.0 µg plasmid DNA in 350 µl HBS followed by 30 min room temperature incubation. The adenovirus-component complexes were of two types; binary complexes that contained adenovirus linked to polylysine-DNA (AdpL) and combination complexes that contained adenovirus plus human transferrin linked to polylysine-DNA (hTfpL/AdpL). The adenoviral component complexes were prepared utilizing the chimeric adenovirus P202 linked to polylysine by an antibody bridge. The reporter plasmid DNA pCLuc4 was used for assays of net gene expression. This plasmid contains the firefly luciferase gene under the transcriptional control of the cytomegalovirus (CMV) enhancer/early promoter. The reporter plasmid DNA pCMVβ was used for assays of localized gene expression. This plasmid contains the bacterial lacZ (β-galactosidase expressing) gene under the transcription control of the CMV enhancer/early promoter.

Gene transfer to primary cultures of cotton rat airway epithelial cells. Cultures of cotton rat airway epithelial cells were prepared by described methods of Van Scott et al. Dissociated cells were harvested, washed three times with F12-7X media, and plated at a density of $5.0 \times 10^5$ cells/dish in 3 cm tissue culture dishes. Cells were maintained in F12-7X media and utilized for gene transfer experiments when they achieved 50–75% confluency. This usually required 2–3 days. For gene transfer experiments, the formed complexes were delivered directly to the cells and incubated for 24 hours. Complexes evaluated included human transferrin-polylysine (hTfpL), adenovirus-polylysine (AdpL), and human transferrin adenovirus-polylysine (hTfpL/AdpL). After incubation, cells were either lysed and evaluated for luciferase gene expression by described methods of Brasier et al. (1989) or stained for β-galactosidase expression utilizing X-gal according to MacGregor and Caskey, 1989. For luciferase assays indicating net gene expression, epithelial cells in primary culture were treated with complexes containing the reporter plasmid DNA pCLuc4 (6.0 µg). For β-galactosidase assays indicating in situ gene expression, cells were treated with complexes containing the reporter plasmid DNA pCMV β(6.0 µg).

Gene transfer to cotton rat airway epithelium in vivo. Formed complexes were delivered to cotton rats via the intratracheal route. For analysis of relative in vivo transfer efficiency, the evaluated complexes included human transferrin-polylysine (hTfpL), adenovirus-polylysine (AdpL), and human transferrin-adenovirus-polylysine (hTfpL/AdpL). These complexes contained the reporter plasmid DNA pCLuc4. For histologic localization of in vivo gene transfer, the human transferrin-adenovirus-polylysine complexes (hTfpL/AdpL) contained the latZ reporter plasmid DNA pCMVβ. Animals were anesthetized with methoxyflurane. After a vertical incision in the ventral aspect of the neck, the trachea was isolated by blunt dissection. With the animal inclined at a 45° angle, the complexes (250–300 µl; 3.0 µg plasmid DNA) were injected directly into the trachea under direct visualization. At indicated times post-injection, the animals were sacrificed by $CO_2$ inhalation and trachea and lung harvested en bloc after perfusion of pulmonary vessels in situ with cold phosphate-buffered saline (PBS). For luciferase assays, the lung blocks were homogenized in extraction buffer, lysates standardized for total protein content and evaluated for luciferase gene expression as described by Brasier et al., 1989. For the β-galactosidase assays, frozen sections of intact unperfused lung were prepared and stained with X-gal as described by MacGregor and Caskey, 1989.

Figures 9, 11:
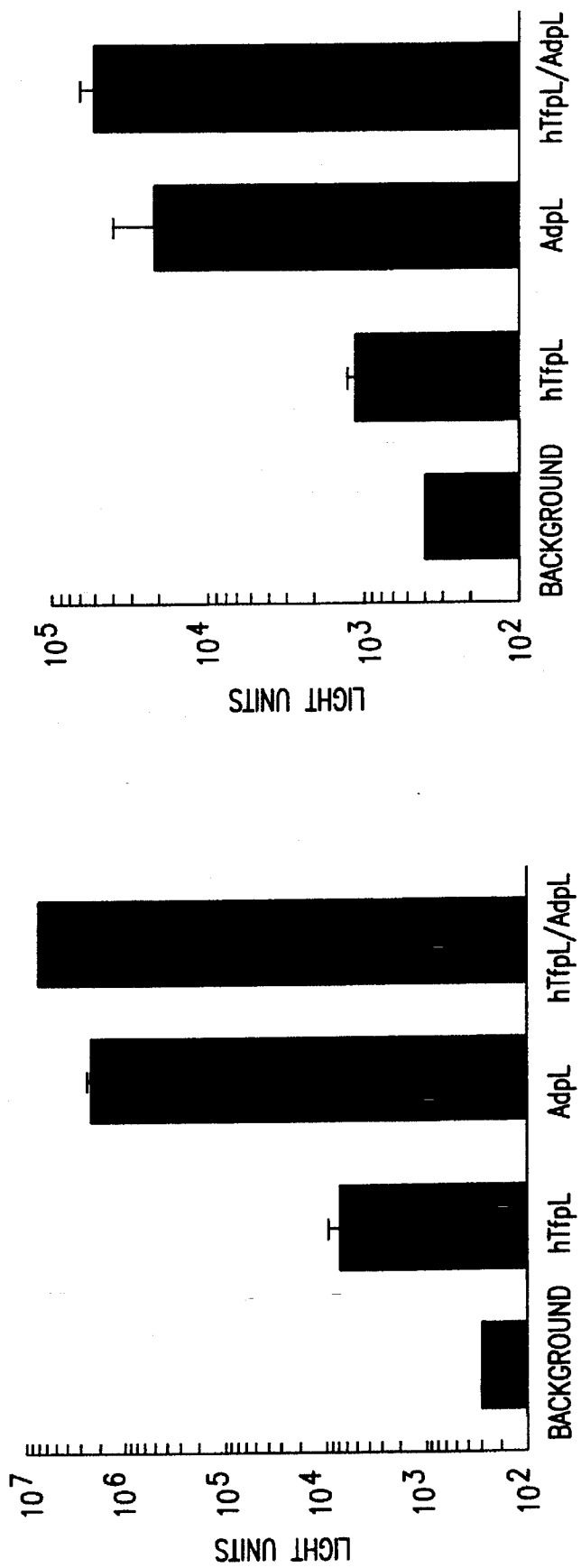
FIG. 9 Relative levels of net gene transfer to cotton rat airway epithelium in primary culture.
FIG. 11 Relative levels of net gene transfer to cotton rat airway epithelium in vivo.

Results
Gene transfer to cotton rat airway epithelial cells in primary culture via receptor-mediated delivery The cotton rat (Sigmodon hispidus) has been shown to be an animal model of human adenoviral lung disease (Pacini et al., 1984) and therefore was employed as a target for gene transfer to respiratory epithelial cells employing adenovirus-polylysine-DNA complexes. The gene transfer efficiency of the various conjugate designs was initially evaluated by transfecting primary cultures of cotton rat airway epithelial cells with a firefly luciferase reporter plasmid pCLuc4 (FIG. 9). The firefly luciferase reporter gene containing plasmid pCLuc4 was used to form conjugate-DNA complexes, which were delivered to airway epithelial cells harvested from rat tracheas. Cell lysates were evaluated for luciferase gene expression after 24 hr. The vector species included human transferrin-polylysine-DNA complexes (hTfpL), adenovirus-polylysine-DNA complexes (AdpL), and human transferrin-adenovirus-polylysine-DNA complexes (hTfpL/AdpL).

FIG. 9 shows the relative levels of net gene transfer to cotton rat airway epithelium in primary culture. Background indicates evaluation of modified cells. Ordinate represents luciferase gene expression as Light Units per 25 µg total protein derived from cellular lysates. Experiments were performed 3–4 times each and results are reported as mean±SEM.

Comparison was made among simple binary complexes that internalize through the transferrin pathway (hTfpL), binary adenoviral-component complexes internalizing via the adenoviral pathway (AdpL), and combination complexes possessing both transferrin and adenoviral domains and thus the capacity to internalize by both pathways (hTfpL/AdpL). In this analysis, the cotton rat airway epithelium in primary culture showed only a very low level of luciferase gene expression employing the hTfpL complexes. This is consistent with the fact that this conjugate species may be entrapped within cellular endosomes owing to the lack of a specific cell vesicle escape mechanism. The adenovirus-component binary complexes (AdpL) exhibited significantly greater gene expression. This was further augmented by the inclusion of a second ligand domain in the combination configuration (hTfpL-AdpL).

Figure 10A:
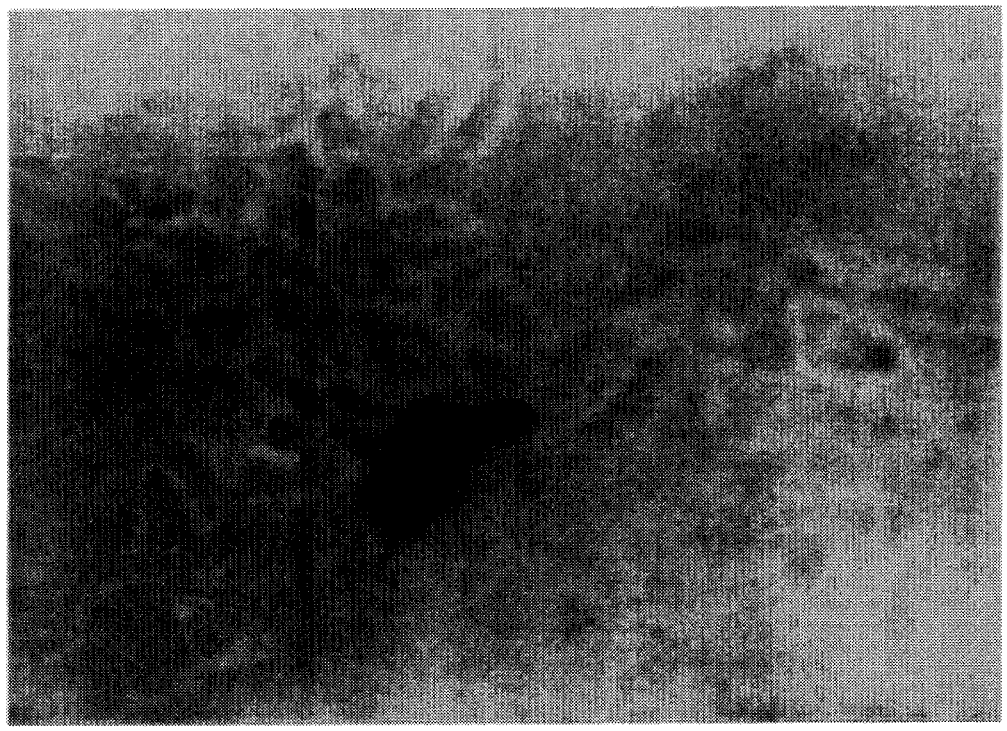
FIGS. 10A, 10B and 10C Relative transduction frequency of cotton rat airway epithelium in primary culture. Results are shown for primary cultures of cotton rat epithelial cells transduced with the various complex species: A.hTfpL; B. AdpL; C. hTfpL/AdpL. Magnification 320X.
Figure 10B:
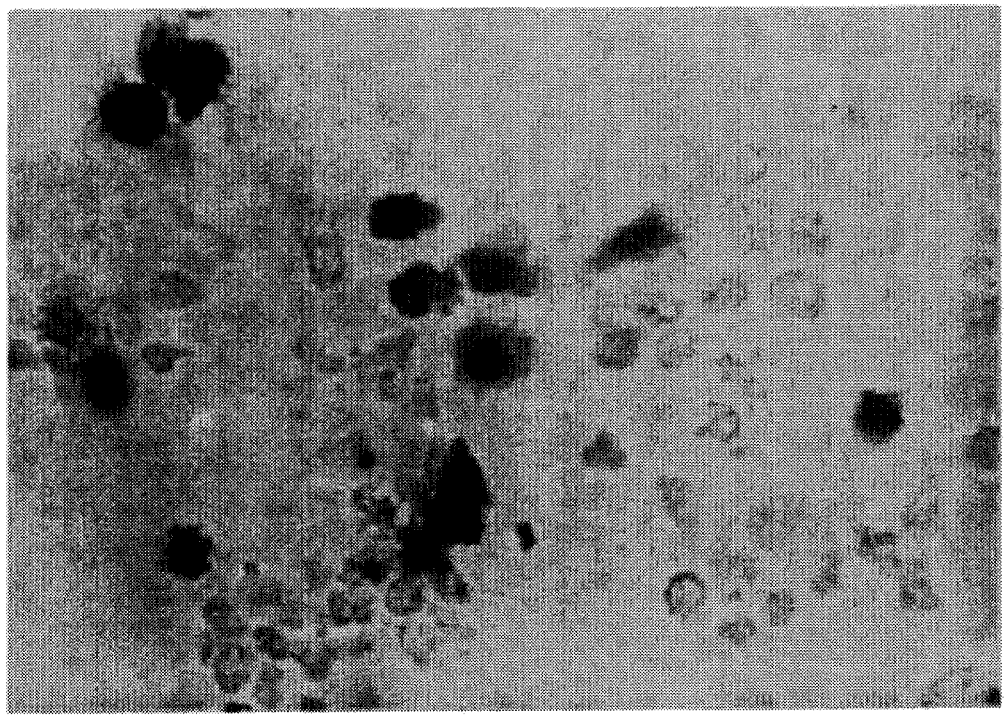
Figure 10C:
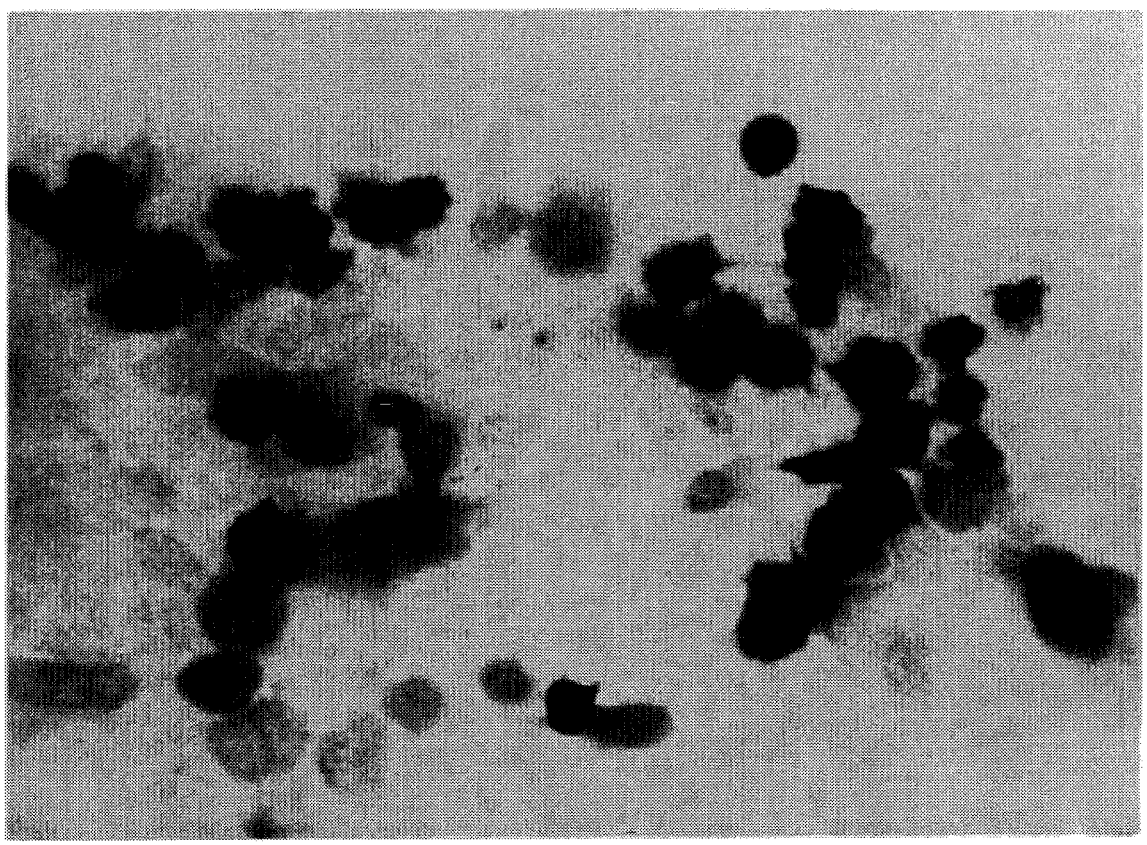
Figure 12A:
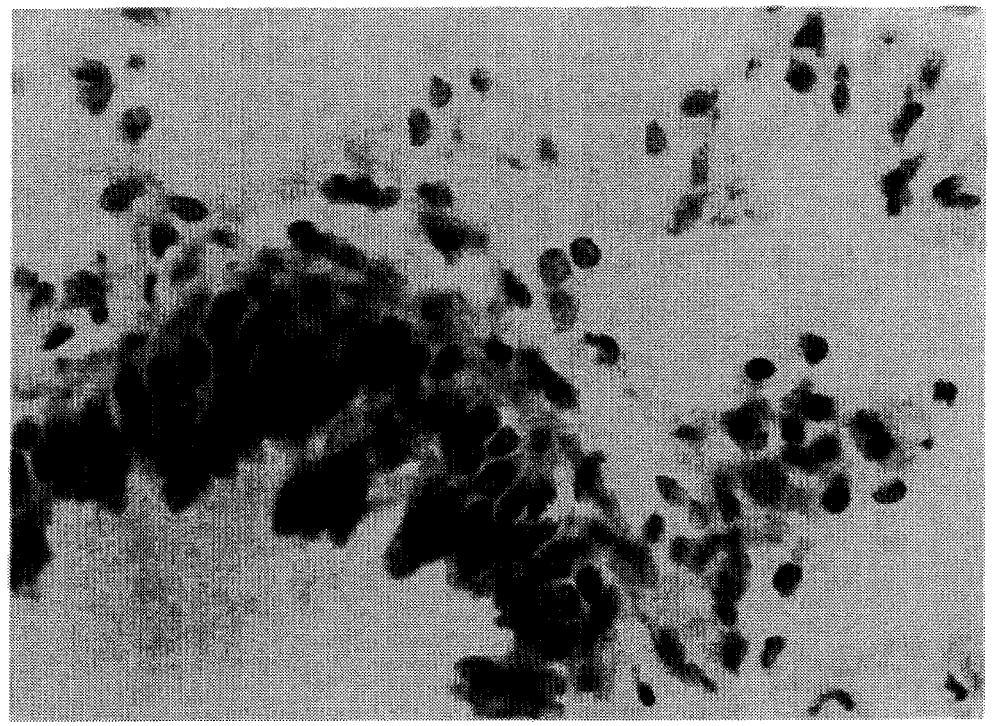
FIGS. 12A, 12B, 12C, 12D and 12E Localization of heterologous gene expression in cotton rat airway epithelium. Results are shown for cotton rats treated with hTfpL/AdpL complexes containing an irrelevant non-lacZ plasmid pRc-RSV or pCMV β containing the lacZ reporter plasmid.
Figure 12B:
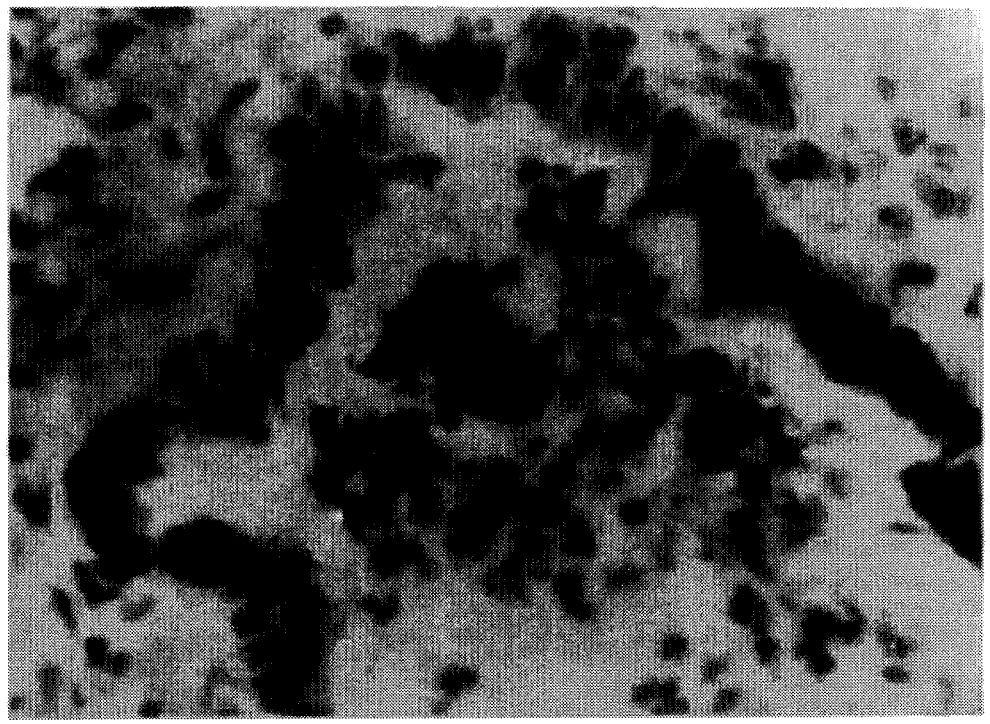
Figure 12C:
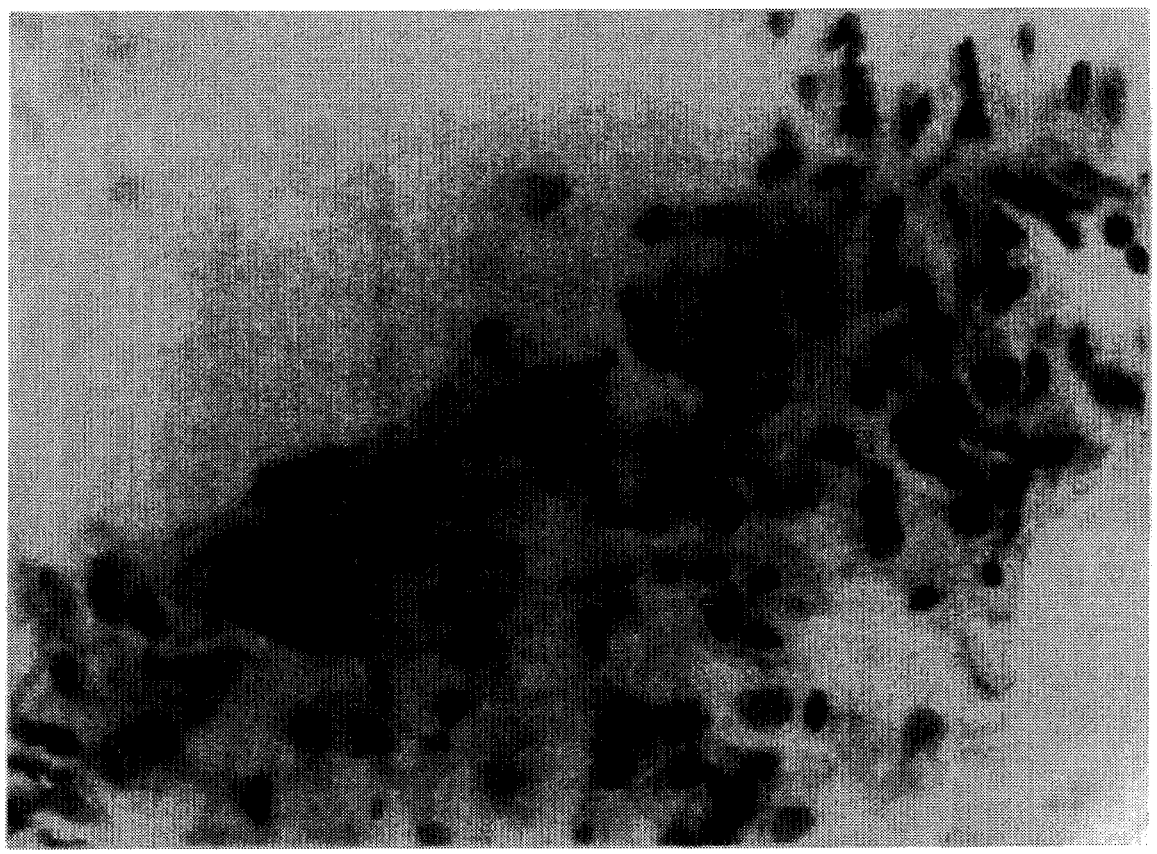
Figure 12D:
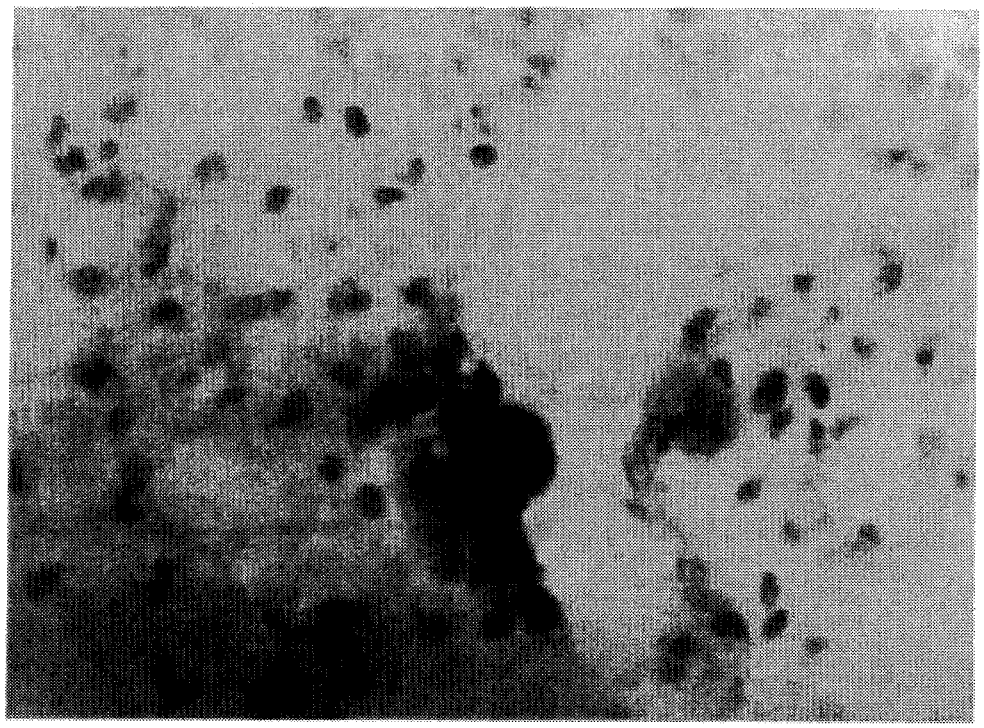
Figure 12E:
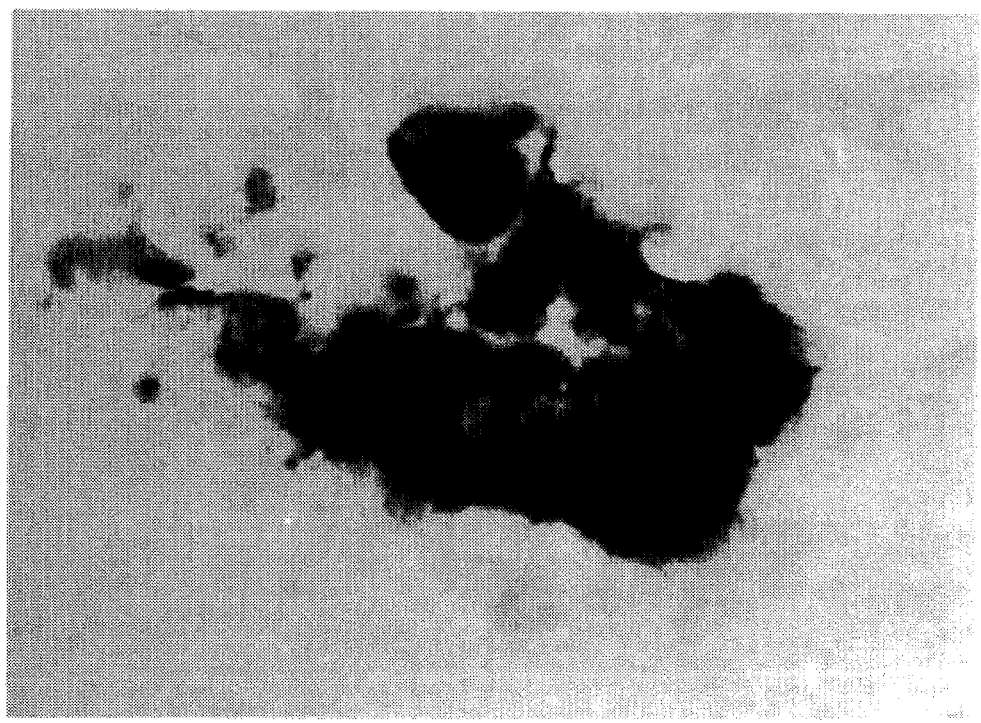

To determine if the relative levels of net gene expression correlated with transduction frequency, the percentage of cells transduced with the various complex species was then determined employing the lacZ histologic reporter plasmid pCMVβ, which encodes the bacterial β-galactosidase gene (FIG. 10). The lacZ histologic reporter containing plasmid pCMVβ was used to form conjugate-DNA complexes and delivered to primary cultures of cotton rat airway epithelia as before. Cells were evaluated for expression of the reporter gene by staining with X-gal at 24 hr.

FIG. 10 shows the relative transduction frequency of cotton rat airway epithelium in primary culture. Results are shown for primary cultures of cotton rat epithelial cells transduced with the various complex species: A. hTfpL; B. AdpL; C. hTfpL/AdpL. Magnification 320×.

In this example, it could be seen that the relative levels of net gene expression observed in the luciferase assay reflected the relative numbers of cells transduced. Thus, the hTfpL-modified airway epithelium in primary culture exhibited 1% transduction frequency, the AdpL complexes on the order of 20–30%, and the hTfpL/AdpL combination complexes greater than 50% modified cells.

Gene transfer to cotton rat airway epithelia in vivo via receptor-mediated delivery The various complex species were next delivered to the airway epithelium of the rodent model by the airway route. Initial evaluation determined the relative in vivo gene transfer efficiency of the complexes employing the luciferase reporter (FIG. 11). The firefly luciferase reporter gene containing plasmid pCLuc4 was used to form conjugate-DNA complexes, which were delivered to cotton rats via injection by the intratracheal route. Lungs were harvested and lysates evaluated for luciferase gene expression after 24 hr. Vector species included human transferrin-polylysine-DNA complexes (hTfpL), adenovirus-polylysine-DNA complexes (AdpL), and human transferrin-adenovirus-polylysine-DNA complexes (hTfpL/AdpL).

FIG. 11 shows the relative levels of net gene transfer to cotton rat airway epithelium in vivo. Background indicates evaluation of lungs from untreated animals. Ordinate represents luciferase gene expression as Light Units per 1250 µg total protein derived from lung lysates. Experiments were performed 3–4 times each and results are expressed as mean±SEM.

In this example, the relative efficiency of the complexes in vivo paralleled the finding in the analysis of primary cultures of airway epithelial cells. Thus, the hTfpL complexes mediated levels of luciferase gene expression in lung extract only slightly above levels observed in unmodified lung. Higher levels were achieved by the AdpL complexes and the highest levels were achieved by the hTfpL/AdpL combination complexes.

The in vivo transduction efficiency employing the lacZ histologic reporter was then evaluated (FIG. 12). The lacZ histologic reporter containing plasmid pCMVβ was used to form human transferrin-adenovirus-polylysine-DNA (hTfpL/AdpL) complexes and delivered to cotton rats via injection by the intratracheal route. At 24 hr, 14 μm thick frozen sections of harvested lungs were evaluated for expression of the reporter gene by stain with X-gal and counterstained with nuclear fast red.

FIG. 12 shows the localization of heterologous gene expression in cotton rat airway epithelium. Results are shown for cotton rats treated with hTfpL/AdpL complexes containing an irrelevant non-lacZ plasmid pRc/RSV or pCMVβ containing the lacZ reporter plasmid. A. Example of bronchlus of cotton rat treated with hTfpL/AdpL completes containing plasmid DNA pRc/RSV; B. Example of bronchus of cotton rat treated with hTfpL/AdpL complexes containing plasmid DNA pCMVβ; C. Example of distal airway region of cotton rat treated with hTfpL/AdpL complexes containing plasmid DNA pRc/RSV; D. Example of distal airway region of cotton rat treated with hTfpL/AdpL complexes containing plasmid DNA pCMVβ. Magnification 600×. E. Enlargement of β-galactosidase positive region from lungs of cotton rat treated with hTfpL/AdpL complexes containing plasmid DNA pCMVβ. Magnification 1000×.

This analysis was limited to the hTfpL/AdpL complex species, which exhibited the highest net in vivo gene transfer. Evaluation of histologic lung sections of animals treated in this manner demonstrated patchy areas of β-galactosidase activity containing multiple marked cells. As a control, no β-galactosidase activity could be detected in animals transduced with the hTfpL/AdpL complexes containing an irrelevant plasmid DNA. These positive regions were localized to the bronchioles and distal airway regions. Specific airway epithelial subsets modified could not be determined in this assay.

Discussion

In this example, the feasibility of accomplishing heterologous gene expression to the respiratory epithelium in situ is demonstrated with adenovirus-polylysine-DNA complexes. Whereas in vivo transduction of airway epithelium has been obtained utilizing other vector systems, adenovirus-polylysine-DNA complexes offer several potential advantages for this application. Practical advantages derive from the fact that this vector system transports heterologous DNA bound to the viral capsid exterior rather than incorporated into the parent virus genome as is the case for recombinant adenoviral vectors (Berkner, K. L., 1988). Thus, the amount of DNA that can be transported is not limited by packaging constraints of the recombinant viral system. Whereas the upper size limit of DNA transportable by recombinant adenoviral vectors is on the order of 6–8 kb (Berkner, K. L., 1988), up to 48 kb of DNA have been transferred utilizing the adenovirus-polylysine-DNA complexes. In addition, the DNA is incorporated into the complexes in a sequence-independent manner. Gene constructs transferred are thus not restricted to the context of viral regulatory controls.

Potential advantages are also offered from a safety standpoint. The production of recombinant adenoviral vectors requires maintenance of the functional integrity of the parent viral genome, since the heterologous sequences are incorporated therein. Despite genetic maneuvers to limit the replicative capacity of the vectors, the E1A/E1B deletion mutants are associated with late viral gene expression and detectable vital replicative capacity (Nevins, J. R., 1981; Gaynor and Berk, 1983; Imperiale et al., 1984. In the configuration of the adenovirus-polylysine-DNA complexes, the entry mechanism of the virus is exploited in a selective manner whereby viral gene elements are not an essential feature. It is thus feasible to inactivate the parent viral genome utilizing a combination of mechanisms, including viral gene deletions and psoralen plus UV-irradiation. By extending this strategy of vector design, it is theoretically possible that viral gene elements may be ultimately eliminated, thereby creating an even safer vector.

The marked plasticity of molecular conjugate design allowed the derivation of a vector with optimized in vivo gene transfer efficiency. The low gene transfer capacity of the hTfpL complexes in vitro and in vivo is consistent with the fact that this species may be entrapped within the cell vesicle system after internalization consequent to the lack of a specific endosome escape mechanism. The AdpL complexes make use of the adenovirus as both ligand domain and endosomolysis principle. These complexes could thus be internalized via adenoviral receptors and escape cell vesicle entrapment by virtue of adenovirus-mediated endosomolysis. This fact was reflected in the significantly augmented gene transfer capacity of these complexes. The addition of a second ligand to the complexes in the hTfpL/AdpL configuration allowed even greater gene transfer to occur both in vitro and in vivo. The fact that these complexes contain two potential ligand domains allows their internalization by both of these pathways. Whereas no direct comparison is made in this study between the in vivo gene transfer efficiency of recombinant adenoviral vectors and adenovirus-polylysine-DNA complexes, it is noteworthy that in the case of the adenovirus-polylysine-DNA complexes the conjugate design may be modified such that it possesses the capacity to internalize both by the adenoviral as well as alternate internalization pathways. A more direct comparison can be made to lipofectin whereby gene expression levels obtained after delivery employing the human transferrin-adenovirus polylysine-DNA complexes were two orders of magnitude greater than levels observed in a similar protocol utilizing the cationic liposomes (Yoshimura et al., 1992).

The detectable in vivo gene expression mediated by the adenovirus-polylysine DNA complexes was of a transient nature. This closely parallels the expression pattern noted after lipofectin-mediated in vivo gene transfer to the respiratory epithelium (Hazinski, et at., 1991). This result is not unanticipated as the delivered DNA would be present as a plasmid episome lacking replicative or integrative capacity (Wilson et al.). In the present design the conjugate system lacks a mechanism to mediate integration and thus the stable transduction frequency would be expected to be low. Alternatively, attrition of the modified cells could explain the extinction of gene transfer in the lung. In terms of the observed transduction frequency, it is hypothesized that the low percentage of cells transduced in vivo could represent a problem of initial binding of the vector to the target airway epithelial cell. In this regard, differentiated airway epithelium may present a vastly different cell surface receptor population than that characterizing immortalized airway epithelial cell lines or primary cultures of airway epithelial cells. Thus, vectors possessing a ligand with a high binding affinity to the differentiated airway epithelium may overcome this problem. In addition, various factors present in the environment of the airway epithelium may be deleterious to vector-mediated gene transfer. These factors include ciliary motion, the bronchial mucus, surfactant, and epithelial lining fluid proteases. To evaluate these possibilities, one may employ various maneuvers to modify the airway epithelial environment prior to vector delivery. These manipulations include: 1) the paralysis of ciliary motion by low temperature or topical anesthesia; 2) dispersal of bronchial mucus through the use of mucolytic agents such as N-acetyl cysteine; and 3) the delivery of inhibitors of proteases to the epithelial lining fluid such as $\alpha_1$-antitrypsin ($\alpha$1AT) and bronchial protease inhibitor (BIP or SLIPI). These various pre-delivery maneuvers can be non-invasively instituted to attempt to mitigate potential in situ barriers to in vivo airway epithelial gene transfer.

Example 7

The Preparation of Chimeric Complexes Containing Adenovirus and the Lectin SNA

Molecular conjugates with the capacity to bind selectively to the ciliated airway epithelial subset may be derived utilizing ligands with known specificity for this cellular target. The construction of these conjugate vectors entails: 1) the confirmation of the binding properties of the candidate ligands in the conjugate confirmation; and 2) the addition of components to enhance internalization after cell-specific binding. The candidate ligands include: 1) influenza virus; 2) the influenza hemagglutinin (HA) glycoprotein; and 3) the lectin SNA (see Piazza, F. M., et al., 1991; and Baum, L. G., et al., 1990). These agents have been demonstrated to bind selectively to ciliated airway epithelial cells. In this experiment, the lectin SNA was employed.

Preparation of the Vector: The chimeric adenovirus P202 ($2.5 \times 10^{10}$ particles) was combined with the antibody-polylysine MP301pL (1.25 µg) in 250 µl HBS and incubated 30 min at room temperature. The reporter plasmid DNA pCLuc4 (6.0 µg) in 125 µl HBS was added and an additional 30 min room temperature incubation was performed. A commercially available biotinylated lectin SNA (E-Y Lab, SanMateo, Calif.; 2.8 µg) in 62.5 µl HBS was combined with streptavidin-polylysine (1.35 µg) in 62.5 µg HBS and incubated for 30 min at room temperature to form SNA-polylysine. The SNA-polylysine was combined with the foregoing reaction mix to form SNA-adenovirus-polylysine-DNA complexes. Complexes lacking the SNA ligand were prepared for comparison. These antibody-linked adenovirus-polylysine-DNA complexes were prepared as previously described.

In vivo transfer of complexes comprising the SNA lectin. The cell-specific tropism of the lectin SNA for human ciliated respiratory epithelium is paralleled in a ferret model. Thus, the ferret was used as an animal target for in vivo gene transfer to the lung. The animals were adult male ferrets of about 1.5 kg. For each animal, the above complexes were prepared in amounts x4. The animals were anesthetized and the complexes delivered to the RML of the lung by bronchoscope. After 24 hr, various lung regions were harvested, homogenized, and analyzed for luciferase activity. The analyzed lung regions included areas not in contact with the complexes during delivery ("left upper airway," "left upper lobe parenchyma," "lower trachea") and regions in contact with the complexes during delivery ("right middle lobe airway," "right middle lobe parenchyma").

Figure 13:
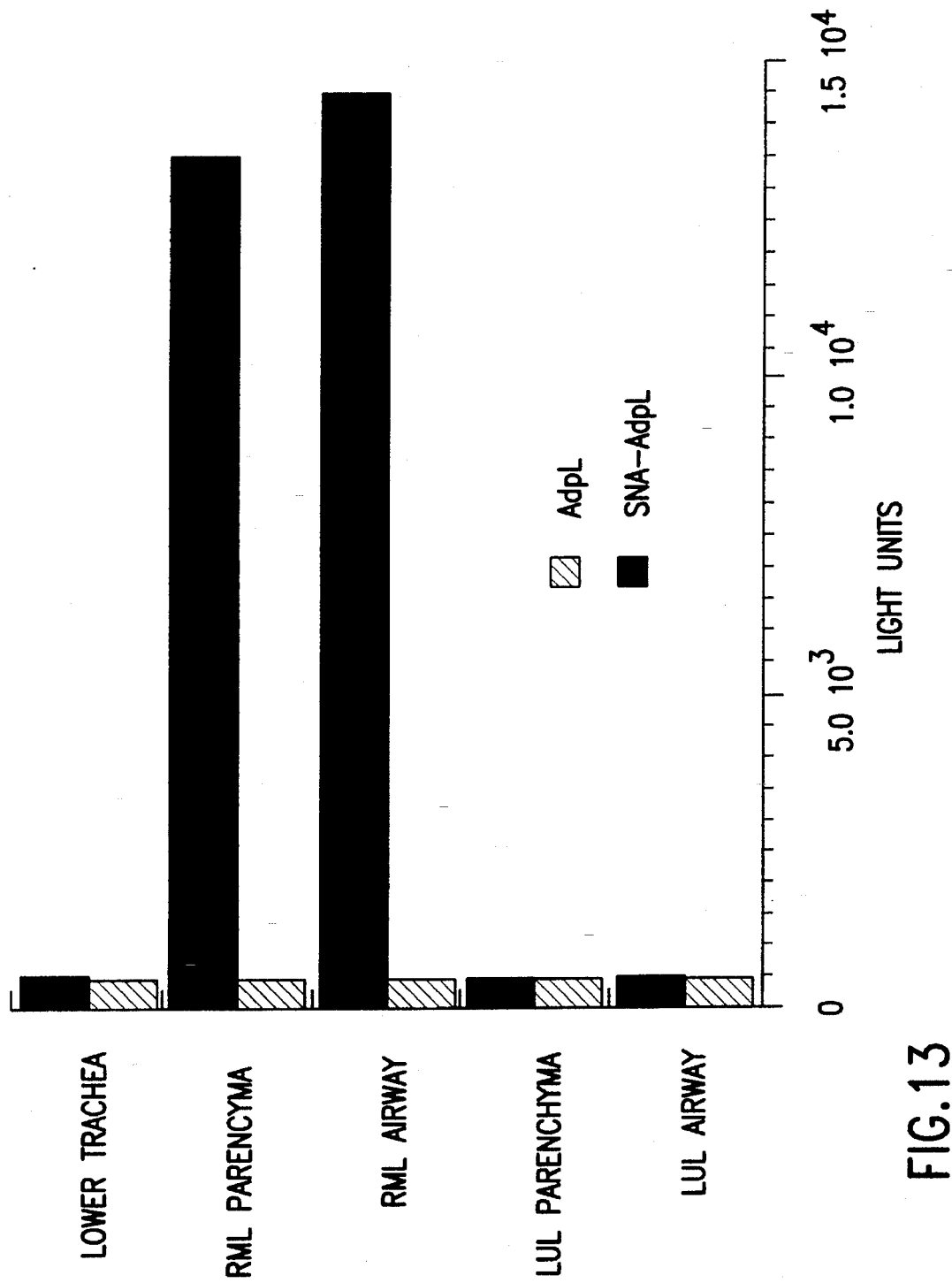
FIG. 13 Transduction of various parts of the ferret lung with complexes with and without the SNA ligand.

As shown in FIG. 13, the complexes comprising the SNA ligand resulted in transfection of those tissues in contact with the complex (RML parenchyma and RML airway).

Example 8

The Preparation of Complexes Containing Influenza Virus Conjugates

Since the CFTR gene is believed to be expressed selectively in the ciliated airway epithelial subset, vector complexes having the ability to target this cell population were developed. To capitalize on the tropism of the influenza HA protein for this subset, an immunologically linked influenza virus-polylysine conjugate was prepared. This conjugate was prepared using a monoclonal antibody having specificity for a nonneutralizing epitope of the virus.

Approximately 0.5 mg of UV-inactivated influenza virus A/PR8 (graciously provided by Peter Palese, Mount Sinai School of Medicine, Department of Microbiology, N.Y., 1.5 min, 10 cm distance) were diluted into 500 µl of F12/DMEM and combined with 2 µg of P4pL (having specificity of the neuraminidase glycoprotein of A/PR8; graciously provided by Dr. Schulman, Department of Microbiology, Mount Sinai School of Medicine, N.Y.) that had been diluted in 250 µl HBS. Incubation was for 30 min at room temperature. Plasmid DNA pRSVL (6.0 µg) in 125 µl of HBS was added to the complexes and incubation continued for 30 min at room temperature. Complete condensation was achieved by dilution of 3 µg poly-Lysine$_{450}$ in 125 µl HBS with incubation as before. Complexes were delivered directly to MDCK cells in 6 cm dishes and incubated at 37° C., 5% $CO_2$ for 24 hr prior to evaluation of cell lysate for luciferase gene expression. Control experiments used P4pL only, A/PR8+ P4pL+ non-lysinated P4 as competitor, A/PR8+ irrelevant antibody-polylysine MP301pL, and irrelevant influenza virus 6131VA.

Figure 14:
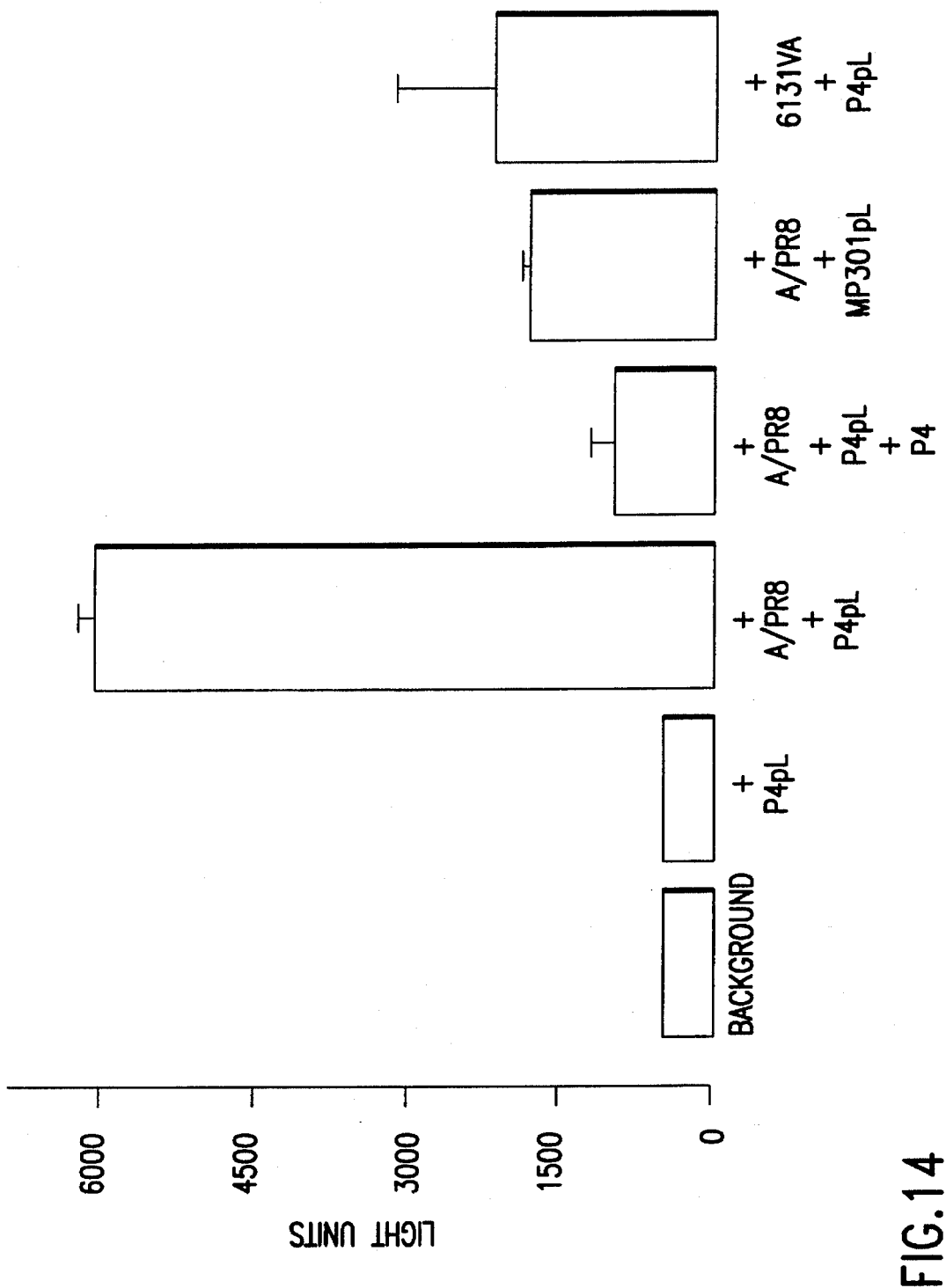
FIG. 14 Evaluation of gene transfer capacity of influenza-polylysine conjugates.

Whereas such a viral polylysine conjugate could be shown to mediate gene transfer to cells susceptible to influenza virus entry (MDCK), the level of gene expression was not as great as for the corresponding adenoviral-polylysine conjugates (FIG. 14). This result may be due to the differing entry pathways of the virons, whereby DNA bound to the surface of the influenza virus would be largely retained in the endosome.

Having now fully described this invention, it will be understood by those of ordinary skill in the art that it can be performed within a wide equivalent range of modes of operation as well as other parameters without affecting the scope of the invention or any embodiment thereof.

Bibliography:

Anderson, W. F., *Science* 226:401–409 (1984)
Anderson, P. et al., *J. Biol. Chem.* 257:11301–11304 (1982)
Abrahamson, D. R. et al., *J. Cell Biol.* 91:270–280 (1981)
Asada-Kubota, M. et al., *Exp. Pathol.* 23:95–101 (1983)
Ascoli, M. et al., *J. Biol. Chem.* 253:7832–7838 (1978)
Ashwell, G. et al., *Annu. Rev. Biochem.* 51:531–554 (1982)
Baum et al., *Acta Histochem. Supp.* 40:35–38 (1990)
Berkner and Sharp, *Nucl. Acids Res.* 11:6003–6020 (1983)
Berkner, K. L., *BioTechniques* 6:616–629 (1988)
Berns, K. I., *Virology*, 2nd Ed., Fields et al., eds., Raven Press Ltd., New York, 1743–1759 (1990)
Brasier et al., *Biotechniques* 7:1116–1122 (1989)
Carpenter, G., *Cell* 37:357–358 (1984)
Cheng, S-Y. et al., *Proc. Natl. Acad. Sci. USA* 77:3425–3429 (1980)
Cotten, M., et al., *Proc. Natl. Acad. Sci. USA* 87:4033–4037 (1990)

Ciliberto, G. et al., *Cell* 41:531–540 (1985)
Clarke et al., *Science* 257:1125–1128 (1992)
Darnell, J., et al., *Mol. Cell Biol.*, Darnell, J., ed., Freeman, New York, 567 (1975)
Davis, B. D. and Dulbecco R., "Sterilization and Disinfection," in *Microbiology*, 3rd Ed., Davis, B. D. et al., eds., Harper & Row, 1264–1274 (1980)
De Wet, J., et al., *Mol. Cell. Biol.* 7:725–737 (1987)
Defer, C., et al., *J. Virol.* 64:3661–3673 (1990)
Dulbecco, R., "The Nature of Viruses," in *Microbiology*, 3rd Ed., Davis, B. D., et al., eds., Harper & Row, 853–884 (1980)
Eglitis and Anderson, *Biotechniques* 6:608–614 (1988)
Felgner, P. L., et al., *Proc. Natl. Acad. Sci. USA* 84:7413–7417 (1987)
Felgner, P. L., et al., *Proc. West. Pharmacol. Soc.* 32:115 (1989)
Fields and Knipe, *Virology*, 2nd edition, Raven Press Ltd., New York (1990)
Gaynor and Berk, *Cell* 33:683–693 (1983)
Ginsberg, H. S., "Picornaviruses," in *Microbiology*, 3rd Edition, Davis, B. D., et al., eds., Harper & Row, 1095–1117 (1980)
Geysen et al., *Proc. Natl. Acad. Sci. USA* 81:3998 (1984)
Geysen et al., *Proc. Natl. Acad. Sci. USA* 82:178 (1985)
Geysen et al., *Mol. Immunol.* 23:709 (1986)
Geysen et al., *J. Immunol. Meth.* 102:259 (1987)
Goldstein, J. L. et al., *Clin. Res.* 30:417–426 (1982)
Goldstein, J. L. et al., *Proc. Natl Acad. Sci. USA* 76:333–337 (1979)
Green, M. et al., *Cell* 58:215–223 (1989)
Hazinski, et al., *Am. J. Respir. Cell. Mol. Biol.* 4:206–209 (1991)
Hearst and Thiry, *Nucl. Acids Res.* 4:1339–1347 (1977)
Heldin, C-H., et al., *J. Biol. Chem.* 257:4216–4221 (1982)
Herskoxicz, I., et al., *Nature* 329:219 (1987)
Hizuka, N., et al., *J. Biol. Chem.* 256:4591–4597 (1981)
Holland, J. J., "Defective Viral Genomes," in *Virology*, 2d Edition, Fields, B. N., et al., eds., Raven Press Ltd., New York, 151–165 (1990)
Horwitz, M. S., "Adenoviridae and Their Replication," in *Virology*, 2d Ed., Fields, B. N., et al., eds., Raven Press Ltd., New York, 1679–1721 (1990)
Hosang, M., et al., *EMBO J.* 6:1197–1202 (1987)
Huang, A. S., "The Role of Defective Interfering (DI) Particles in Viral Infection," in *The Molecular Basis of Viral Replication*, Hsg. Bercoff, R. P., Plenum Press, New York and London, 191–194 (1987)
Huebers and Finch, *Physiol. Rev.* 67:520–582 (1987)
Hu, P. C., et al., *J. Exp. Med.* 145:1328–1343 (1977)
Imperiale et al., *Mol. Cell. Biol.* 4:867–874 (1984)
Imamura, K. et al., *J. Immunol.* 139:2989–2992 (1987)
Inamine, J. M., et al., *Gene* 73:175–183 (1988)
Kaplan, J. et al., *J. Biol. Chem.* 254:7323–7328 (1979)
Klausner, R. D. et al., *J. Biol. Chem.* 258:4715–4724 (1983)
Klausner, R. D. et al., *Proc. Natl. Acad. Sci. USA* 80:2263–2266 (1983)
Kuhn, L. C. et al., *Trends Biochem. Sci.* 7:299–302 (1982)
Kunkel, T. A., *Proc. Natl. Acad. Sci. USA* 82:488–492 (1985)
Kurachi, K. et al., *Proc. Natl. Acad. Sci. USA* 79:6461–6464 (1982)
Ledley, F. D. et al., *Biotechnology*, Vol. 7b H-J (Rehm and Reed, eds., VCH Verlagsgesellschaft, Weinheim, pp. 401–457 (1989)
Loyter, A., et al., *Proc. Natl. Acad. Sci. USA* 79:422 (1982)
MacGregor and Caskey, *Nucleic Acids Res.* 17:2365 (1989)
Malim, M. et al., *Cell* 58:205–214 (1989)
Malone, R. W., et al., *Proc. Natl. Acad. Sci. USA* 86:6077 (1989)
Maniatis, T., et al., *Molecular Cloning: A Laboratory Manual*, Cold Spring Harbor Laboratory, Cold Spring Harbor, N.Y., 474 (1982)
Marshall, S., *J. Biol. Chem.* 250:4133–4144 (1985)
Massague, J. et al., *J. Cell. Physiol.* 128:216–222 (1986)
Maurer, R. A., *Focus* 11:25 (1989)
McClure, M. O., et al., *J. General Virol.* 71:767–773 (1990)
Mellman, I. S. et al., *J. Cell Biol.*, 98:1170–1177 (1984)
Mizel, S. B. et al., *J. Immunol.* 138:2906–2912 (1987)
Nevins, J. R., *Cell* 26:213–220 (1981)
Pacini et al., *J. Infect. Dis.* 150:92–97 (1984)
Pastan, I., et al., *Virus Attachment and Entry into Cells*, Crowell and Lonberg-Holm, eds., Am. Soc. for Microbiol., Washington, D.C., 141–146 (1986)
Philipson, L., et al., *J. Virol.* 2:1064–1075 (1968)
Philipson, L., *Curr. Top. Microbiol. Immunol.* 109:2 (1983)
Piazza et al., *Am. J. Respir. Cell Mol. Biol.* 4:82–87 (1991)
Ponder, K. P. et al., *Proc. Natl. Acad. Sci. USA* 88:1217–1221 (1991)
Posner, B. I. et al., *J. Cell Biol.* 93:560–567 (1982)
Precious and Russell, *Virology: A Practical Approach*, B. W. J. Mahy, ed., IRL Press, Oxford, Washington, D.C., pp. 193–205 (1985)
Roberts, M. M. et al., *Science* 232:1148–1151 (1986)
Russell, W. C. et al., *J. Gen. Virol.* 56:393–408 (1981)
Riordan, J. R. et al., *Science* 245:1066–1073 (1989)
Schalch, D. S. et al., *Endocrinology* 118:1590–1597 (1986)
Sennett, C. et al., *Annu. Rev. Biochem.* 50:1053–1086 (1981)
Seth et al., *Mol. Cell. Biol.* 4:1528–1533 (1984)
Sly, W. et al., *J. Cell Biochem.* 18:67–85 (1982)
Smith, K. A. et al., *Proc. Natl. Acad. Sci. USA* 82:864–867 (1985)
Stahl, P. D. et al., *Proc. Natl. Acad. Sci. USA* 75:1399–1403 (1978)
Sullenger, B. A. et al., *Cell* 63:601–608 (1990)
Svensson, U., *J. Virol.* 55:442–449 (1985)
Trono, D. et al., *Cell* 59:113–120 (1989)
Uchida, Y., et al., *J. Biochem.* 82:1425–1433 (1977)
Valerio, D. et al., *Gene* 31:147–153 (1984)
Van Scott et al., *Exp. Lung Res.* 11:75–94 (1986)
Wagner, E., et al., *Proc. Natl. Acad. Sci. USA* 87:3410–3414 (1990)
Wagner, E., et al., *Proc. Natl. Acad. Sci. USA* 88:4255–4259 (1991a)
Walker, F. et al., *J. Cell Physiol.* 130:255–261 (1987)
Willumsen J. J., et al., *Am. J. Physiol.* 256:C1033–C1044 (1989)
Wagner, E., et al., *Bioconjugate Chemistry* 2:226–231 (1991b)
Wilson et al., *J. Biol. Chem.* 267:11483–11489 (___)
Wood, W. I. et al., *Nature* 312:330–337 (1984)
Wu, G. Y. and Wu, C. H., *J. Biol. Chem.* 262:4429–4432 (1987)

We claim:

1. An adenovirus conjugate which is capable of forming a complex with a nucleic acid and delivering said nucleic acid into the cytoplasm of a higher eukaryotic cell by endosomolysis, said adenovirus conjugate comprising an adenovirus capable of endosomolysis, which is bound to an antibody through a specific antigen/antibody bond wherein said antibody is covalently bound to a polycation having affinity for a nucleic acid, and wherein said conjugate is internalized into an endosome of a higher eukaryotic cell via receptor mediated endocytosis and said nucleic acid is released into the cytoplasm of the higher eukaryotic cell via endosomolysis which is mediated by the adenovirus.

2. The adenovirus conjugate according to claim 1, wherein said adenovirus internalizes said conjugate into said higher eukaryotic cell.

3. The adenovirus conjugate according to claim 1, characterized in that the adenovirus comprises a hexon protein and the antibody binds to an epitope in the hexon protein.

4. The adenovirus conjugate according to claim 3, characterized in that the adenovirus is a chimeric virus which contains in the sequence coding for the hexon protein, in place of the codons 188 to 194, the sequence coding for amino acids 914 to 928 of the *Mycoplasma pneumoniae* protein P1 and that the antibody binds through specific antibody/antigen binding to the P1 region.

5. The adenovirus conjugate according to claim 1, characterized in that the polycation is polylysine.

6. The adenovirus conjugate according to claim 2, characterized in that the antibody is a monoclonal antibody.

7. A complex of a nucleic acid and the conjugate of claim 1.

8. The complex according to claim 7, characterized in that the adenovirus internalizes said complex into said higher eukaryotic cell.

9. The complex according to claim 7, characterized in that said complex further comprises a second conjugate of an internalizing factor covalently bound to a organic polycation having an affinity for nucleic acid, said internalizing factor being specific for a surface receptor of a higher eukaryotic cell, wherein said adenovirus conjugate and said second conjugate are complexed with said nucleic acid.

10. The complex according to claim 7, wherein said polycation is polylysine.

11. The complex according to claim 9, characterized in that the internalizing factor of the second conjugate is transferrin.

12. The complex according to claim 7, characterized in that the complex further comprises an internalizing factor.

13. A transfection kit, comprising a carrier means having in close confinement therein two or more container means, wherein a first container means contains a conjugate comprising a polycation having affinity for a nucleic acid bound to an antibody, and a second container means which contains an adenovirus to which the antibody of the first container means is capable of binding wherein said adenovirus (a) is capable of being internalized into an endosome of a higher eucaryotic cell when it is part of a complex comprising:
  (i) said polycation having affinity for a nucleic acid and
  (ii) a nucleic acid; and wherein said adenovirus
(b) causes the release of the contents of the endosome of the higher eucaryotic cell into the cytoplasm of the higher eucaryotic cell by endosomolysis.

14. A transfection kit, comprising a carrier means having in close confinement therein one or more container means, wherein a container means contains a conjugate comprising a polycation having affinity for a nucleic acid which is bound via an antibody to an adenovirus, wherein said adenovirus (a) is capable of being internalized into an endosome of a higher eucaryotic cell when it is part of a complex comprising
  (i) said polycation having affinity for a nucleic acid and
  (ii) a nucleic acid; and wherein said adenovirus
(b) causes release of the contents of the endosome of said higher eucaryotic cell into the cytoplasm of said higher eucaryotic cell by endosomolysis.

15. The transfection kit of claims 13 or 14, wherein one of said vials further comprises a second conjugate of an internalizing factor for a higher eucaryotic cell covalently bound to a polycation having affinity for a nucleic acid.

* * * * *

UNITED STATES PATENT AND TRADEMARK OFFICE
CERTIFICATE OF CORRECTION

PATENT NO. : 5,521,291

DATED : May 28, 1996

INVENTOR(S): Curiel *et al.*

It is certified that an error appears in the above-identified patent and that said Letters Patent is hereby corrected as shown below.

In column 36, at line 26, delete "vials" and insert therein --container means--.

Signed and Sealed this

Third Day of December, 1996

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCTGAGCAGC AA         12

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GTCGAAGGTC AAACACCTAA A         21

( 2 ) INFORMATION FOR SEQ ID NO:3:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TCAACTACTG AGGCGACCGC AGGCAATGGT GATAACTTGA CT         42

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CTTACCAAGG TAAAACCTAA AACAGGTCAG GAAAATGGA         39